US007256180B2

(12) United States Patent
Kabanov et al.

(10) Patent No.: US 7,256,180 B2
(45) Date of Patent: *Aug. 14, 2007

(54) COMPOSITIONS AND METHODS FOR INDUCING ACTIVATION OF DENDRITIC CELLS

(75) Inventors: Alexander V. Kabanov, Omaha, NE (US); Pierre Lemieux, St. Therese (CA); Valery Alakhov, Baie D'Urfe (CA); Nadia Guerin, Longueuil (CA)

(73) Assignee: Supratek Pharma Inc., Quebec (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/845,938

(22) Filed: Apr. 30, 2001

(65) Prior Publication Data

US 2003/0118550 A1 Jun. 26, 2003

Related U.S. Application Data

(60) Provisional application No. 60/260,806, filed on Jan. 10, 2001, provisional application No. 60/200,487, filed on Apr. 28, 2000.

(51) Int. Cl.
A61K 48/00 (2006.01)
A61K 9/127 (2006.01)

(52) U.S. Cl. .................. 514/44; 424/450; 435/455

(58) Field of Classification Search .............. 435/4; 436/66, 43; 422/63, 67, 73; 514/44; 424/486, 424/422; 800/8–13
See application file for complete search history.

(56) References Cited

U.S. PATENT DOCUMENTS

| 4,027,013 | A | | 5/1977 | Bick et al. | |
| 4,188,373 | A | | 2/1980 | Krezanoski | |
| 4,609,546 | A | | 9/1986 | Hiratani | |
| 4,740,498 | A | | 4/1988 | Hirao et al. | |
| 4,772,466 | A | | 9/1988 | Allison et al. | |
| 5,412,072 | A | | 5/1995 | Sakurai et al. | |
| 5,417,982 | A | | 5/1995 | Modi | |
| 5,436,170 | A | | 7/1995 | Cornell et al. | |
| 5,449,513 | A | | 9/1995 | Yokoyama et al. | |
| 5,554,372 | A | | 9/1996 | Hunter | |
| 5,648,071 | A | | 7/1997 | Hunter et al. | |
| 5,656,611 | A | | 8/1997 | Kabanov et al. | |
| 5,696,090 | A | | 12/1997 | McGregor et al. | |
| 5,830,877 | A | * | 11/1998 | Carson et al. | 514/44 |
| 5,840,319 | A | | 11/1998 | Alakhov et al. | |
| 5,885,590 | A | | 3/1999 | Hunter et al. | |
| 6,218,438 | B1 | * | 4/2001 | Alakhov et al. | 514/772.4 |
| 6,277,410 | B1 | | 8/2001 | Kabanov et al. | |
| 6,359,054 | B1 | * | 3/2002 | Lemieux et al. | 524/505 |
| 6,387,406 | B1 | * | 5/2002 | Kabanov et al. | 424/486 |
| 6,589,940 | B1 | * | 7/2003 | Raz et al. | 514/44 |
| 6,656,459 | B2 | * | 12/2003 | Kabanov et al. | 424/78.03 |
| 6,677,313 | B1 | * | 1/2004 | Mathiowitz et al. | 514/44 |
| 2002/0019358 | A1 | * | 2/2002 | Manthorpe et al. | 514/44 |

FOREIGN PATENT DOCUMENTS

| EP | 0 211 601 A2 | 7/1986 |
| WO | WO92/00101 | 1/1992 |
| WO | WO 96/15778 | 5/1996 |
| WO | WO 96/16541 | 6/1996 |
| WO | WO 96/40055 | 12/1996 |
| WO | WO 96/40056 | 12/1996 |
| WO | WO 99/39731 | 8/1999 |

OTHER PUBLICATIONS

Jakob et al, J Immunol 1998;1998;161:3042-9.*
Denis-Mize et al, Gene Ther. Dec. 2000;7:2105-12.*
Alexander V. Klabanov et al., A New Class of Drug Carriers: Micelles of Poly (oxyethylene)-poly (oxypropylene) Block Copolymers as Microcontainers for Drug Targeting From Blood in Brain, Journal of Controlled Release 22:141-158 (1992).
Alexander V. Klabanov et al., Interpolyelectrolyte and Block Ionomer Complexes for Gene Delivery: Physico-chemical Aspects, Advanced Drug Delivery Reviews, 30:49-60 (1998).
Elena V. Batrakova et al., Effects of Pluronic Block Copolymers on Drug Absorption in Caco-2 Cell Monolayers, Pharmaceutical Research, vol. 15, No. 6, pp. 850 (1998).
Vladimir P. Chekhonin et al., Fatty Acid Acylated Fab-fragments of Antibodies to Neurospecific Proteins as Carriers for Neuroleptic Targeted Delivery in Brain, FEBS 287, pp. 149-152 (1991).
Devery A. Howerton et al. Inductin of Macrophage Ia Expression in Vivo by a Synthetic Block Copolymer, L81, Journal of Immunology, vol. 144, pp. 1578-1584 (1990).
Otmane Boussif et al. , A Versatile Vector for Gene and Oligonucleotide Transfer Into Cells In Culture and In Vivo: Polyethylenimine, Proc. Natl. Acad. Sci. USA, vol. 92, pp. 7297-7301 (1995).

(Continued)

Primary Examiner—Q. Janice Li
(74) Attorney, Agent, or Firm—Mathews, Shepherd, McKay & Bruneau, P.A.

(57) ABSTRACT

Compositions induce the activation of dendritic cells comprising a polynucleotide, such as viruses, RNA, DNA, plasmid DNA, or derivatives thereof and at least one block copolymer of alkylethers. The present invention further relates to compositions for inducing the activation of dendritic cells wherein the block copolymers are PLURONIC F127 and L61. More particular, the compositions comprise block copolymers PLURONIC F127/PLURONIC L61. The invention also relates to methods of inducing the activation of dendritic cells in animals comprising administering the compositions of the invention. Additionally, the present invention relates to methods of increasing the immune response of animals comprising administering the compositions of the present invention.

12 Claims, No Drawings

OTHER PUBLICATIONS

James G. McArthur et al., Induction of Protective Anti-Tumor Immunity by Gene-Modified Dendritic Cells, Journal of Immunotherapy, 21(1): 41-47 (1998).

H-K Nguyen et al., Evaluation of Polyether-Polyethyleneimine Graft Copolymers as Gene Transfer Agents, Gene Therapy (2000) 7, pp. 126-138 (2000).

* cited by examiner

COMPOSITIONS AND METHODS FOR INDUCING ACTIVATION OF DENDRITIC CELLS

CROSS REFERENCE TO RELATED APPLICATION

This application claims the benefit of U.S. Provisional patent application Ser. No. 60/200,487, filed Apr. 28, 2000 and U.S. Provisional Patent Application Ser. No. 60/260,806, filed Jan. 10, 2001.

FIELD OF THE INVENTION

The invention relates to compositions and methods for activation of dendritic cells by administering compositions comprising polynucleotides, such as viruses, RNA, DNA, or derivatives thereof, and at least one block copolymer of an alkyether.

BACKGROUND OF THE INVENTION

Vaccination is an efficient way of preventing death or disability from infectious diseases. The success of this method in the field of infectious disease has also stimulated interest in utilizing vaccination in the treatment or prevention of neoplastic disease. Despite the successes achieved with the use of vaccines, however, there are still many challanges in the field of vaccine development. Parenteral routes of administration, the numbers of different vaccinations required and the need for, and frequency of, booster immunizations all impede efforts or eliminate disease.

One such difficulty is lack of immunogenicity, i.e., the antigen is unable to promote an effective immune response against the pathogen. In addition, certain antigens may elicit only a certain type of immune response, for example, a cell-mediated or a humoral response. Adjuvants are substances that enhance, augment or potentiate an immune response, and can in some instances, be used to promote one type of immune response over another. Although numerous vaccine adjuvants are known, aluminum salt is the only adjuvant widely used in humans, not, however, without any safety concern.

There is now convincing evidence that the immune system can recognize, and in some cases destroy, malignant cells and infectious agents. Furthermore, T cells, and in particular CD8+ cytotoxic T lymphocytes (CTLs), appear to be the principal affectors of anti-tumor and anti-infectious disease immunity. Activation of T cells is known to be dependent on dendritic cells. Dendritic cells (DC) are unique among antigen presenting cells (APC) by virtue of their potent capacity to activate immunologically naive T cells (Steinman, 1991). DC express constitutively, or after maturation, several molecules that mediate physical interaction with and deliver activation signals to responding T cells. These include class I and class II MHC molecules. CDSO (B7-1) and CD86 (B7-2); CD 40; CD11a/CD18 (LFA-1); and CD54 (ICAM-1) (Steinman, 1991; Steinman et al. 1995). The unique ability of dendritic cells to present antigens and to activate naive and memory CD4+ and CD8+ T cells provides the possibility of using them to trigger specific anti-tumor immunity. Therefore, an agent that could selectively induce dendritic cells and increase their ability to stimulate immune response would be of wide importance. Numerous studies have shown a high potency of dendritic cell-based vaccines for cancer immunotherapy in animal models, some have been carried out against human cancers in clinical trials. Human tumors express a number of protein antigens that can be recognized by cytotoxin lymphocytes (CTL), thus providing potential targets for cancer immunotherapy.

Dendritic cells (DCs) are rare leukocytes that are uniquely potent in their ability to present antigens to T cells, and this property has promoted their recent application to therapeutic cancer vaccines. Other cells are also known to be able to present antigens such as macrophages and B-cells. However, macrophages cannot take up soluble antigens efficiently, while immature dendritic cells can take up large amount of antigen from extracellular fluid by macropinocytosis.

B-cells, by contrast, are uniquely adapted to bind specific soluble molecules through their cell-surface immunoglobulin. B-cells internalize the soluble antigen bound by their immunoglobulin receptors and then display peptide fragments of these antigens as peptides: MHC class II complexes. The problem with B-cells is that they do not constitutively express co-stimulatory activity. Although B-cells efficiently present soluble proteins, they are unlikely to initiate a potent CTL response in the absence of co-stimulatory activity. As a result the antigen not only fails to activate naive T-cells, but causes them to become anergic, or non-responsive.

Isolated DCs loaded with tumor antigen ex vivo and administered as a cellular vaccine have been found to induce protective and therapeutic anti-tumor immunity in experimental animals. In pilot clinical trials of DC vaccination for patients with non-Hodgkin's lymphona and melanoma, induction of anti-tumor immune responses and tumor regressions have been observed. Timmerman et al., *Annal, Rev Med* 1999, 50:507-29; Tarte et al., *Leukemia*, 13:653-663 (1999). Additional trials of DC vaccination for a variety of human cancers are under way, and methods for targeting tumor antigens to DCs in vivo are also being explored. Exploitation of the antigen-presenting properties of DCs thus offers new possibilities for the development of effective cancer immunotherapies. Therefore, DCs can be used as a cell vaccine, but they can also be used as an immunomodulating factor in combination with DNA vaccine. Following DNA vaccination, DCs efficiently present vaccine-encoded antigens. Casares et al., *J. Exp. Med.*, 186(9):1481-6 (1997). Plasmid DNA has an adjuvant effect that promotes DC maturation and migration to lymphoid tissue. However, only a very low number of DCs are usually transfected with a direct injection of plasmid DNA, and a very low number of DCs migrate to the site of injection. Lane et al., *Immunology*, 11:308-313 (1999). The expression of antigen by directly tranfected DCs become undectable after 2 weeks, but memory CD4+ T cell responses are maintained over 40 weeks, questioning the role of persistent antigen in maintaining CD4+ T cell memory. Bacterial DNA (CpG motifs) induces maturation of Langerhans cells and of immature bone-marrow-derived DCs. Bacterially-derived lipopolysaccharide (LPS) has long been known to be an activator for DCs. By triggering a Th1-type response, not only can inflammatory T cells be recruited to sites of infection in order to activate macrophages, but also they attract neutrophils to the infected area by secreting chemokines.

Co-delivery of the GM-CSF adjuvant and glycoprotein D antigen boosts immune response during plasmid DNA vaccination with naked DNA. Flo et al., *Vaccine*, 18(28): 3242-53 (2000). Gene delivery has been used to express cytokines (interleukin-12) through the use of plasmid DNA encoding cytokines with poly(α-4-aminobutylglycolic acid) complexes. Maheshwari et al., *Mol. Ther.*, 2(2): 121-130.

(2000). The tumor suppressor (antigen) p53 and interleukin12 (as well as TNF-α and IFNγ) have been administered via gene delivery in a gene delivery system named "LPD" to initiate cytokine response and inhibit tumor growth. Whitmore et al., *Gene Ther.*, 6(11) 1867-75 (1999). Intravenous injection of plasmids encoding the human FLT-3 ligand increase the number of functional and natural killer cells (NK). He et al., *Hum. Gene Ther.*, 11(4): 547-54 (2000). Several workers have used FLT-3 to boost gene expression during a retroviral-mediated gene therapy. Murray et al., *Hum. Gene Ther.*, 10(11): 1743-52 (1999) and Goerner et al., *Blood*, 94(7): 2287-92 (1999). FLT-3, as well as GM-CSF, has been used to induce development of dendritic cells and boost gene expression during a retrovirus-mediated gene vaccination therapy. Mach et al., *Cancer Res.*, 60(12): 3239-46 (2000). CD40 and FLT-3 ligands induce dendritic cells and boost gene expression during a retrovirus-mediated gene vaccination therapy. Borges et al., *J. Immunol.* 163(3) 1289-97 (1999).

The present invention relates to compositions comprising polynucleotides, such as plasmid DNA, DNA, RNA, viruses or vectors, and at least one block copolymer that induce an increased level of production and infiltration of DCs in response to the expression of the gene product encoded by the above DNA, in particular plasmid DNA. This event leads to a higher immune response against an encoded exogenous antigen (transgene), and a better humoral and cellular immune reponse is acheived. The compositions of the present invention can also be used to generate large amount of dendritic cells both in vitro and in vivo. The current methods of generation, stimulation, and maturation of DCs are extremely difficult and tedious, while the present invention significantly simplifies the process.

Direct injection of naked plasmid DNA either intramuscularly or intradermally induces strong, long-lived immune responses to the antigen encoded by the DNA vaccines. Both routes of immunization lead to production of specific antibodies and the activation of both MHC class I-restricted, antigen-specific CTL and MHC class II-restricted Th cells secreting Th1-type cytokines (Genetic vaccines, *Scientific Amer.*, July 1999, pp. 50-57). These properties have made plasmid DNA vaccines an attractive alternative to conventional immunizations using proteins, live attenuated viruses or killed whole organisms. Consequently, DNA vaccines are actively being investigated as therapies or preventive measures in such diverse areas as infectious diseases, allergies, and cancers. Despite the avid interest in this method of immunization, DNA vaccines are limited by the capacity to express the protein. An efficient immunization is dependent upon gene expression, which means that the DNA vaccines have to express the protein.

The unique features of smooth, skeletal, and cardiac muscles, have presented numerous challenges for the development and administration of effective polynucleotide compositions for intramuscular administration. Direct injection of purified plasmids ("naked DNA") in isotonic saline into muscle was found to result in DNA uptake and gene expression in smooth, skeletal, and cardiac muscles of various species. Rolland A., *Critical Reviews in Therapeutic Drug Carrier Systems*, Begell House, 143 (1998). It is believed that the unique cytoarchitectural features of muscle tissue are responsible for the uptake of polynucleotides because skeletal and cardiac muscle cells appear to be better suited to take-up and express injected foreign DNA vectors relative to other types of tissues. Dowty & Wolff, *Gene Therapeutics: Methods and Applications of Direct Gene Transfer*, Birkhäuser, Boston, p. 182 (1994). The relatively low expression levels attained by this method, however, have limited its applications. See Aihara and Miyazaki, *Nature Biotechnology*, 16:867 (1998). Additionally, traditional gene delivery systems such as polycations, cationic liposomes, and lipids that are commonly proposed to boost gene expression in other tissues usually result in inhibition of gene expression in skeletal and cardiac muscles. Dowty & Wolff, loc. cit., p. 82 (1994).

Even if the muscle is known to be the only tissue that efficiently takes up and expresses plasmid DNA in the absence of a viral vector, the muscle is not considered to be a site for antigen presentation because it contains few if any dendritic cells, macrophages, and lymphocytes. The skin and mucous membranes are the anatomical sites where most exogenous antigens are normally encountered. The skin-associated lymphoid tissue contain specialized cells that enhance immune responses. Raz et al., *PNAS*, 91: 9519-9523 (1994).

Anionic polymers such as dextran sulfate and salmon DNA can decrease gene expression in the muscle. Rolland A., Loc. cit. Various noncondensive interactive polymers have been used with a limited success to modify gene expression in striated muscle. Nonionic polymers such as poly(vinyl pyrrolidone) poly(vinyl alcohol) interact with plasmids through hydrogen bonding. Id. These polymers may facilitate the uptake of polynucleotides in muscle cells and cause up to 10-fold enhancement of gene expression. However, to achieve a significant increase in gene expression, high concentrations of polymers (about 5% and more) need to be administered. Mumper et al., *Pharmacol. Res.*, 13, 701-709 (1996); March et al., *Human Gene Therapy*, 6(1), 41-53 (1995). This high concentration of poly(vinyl pyrrolidone) poly(vinyl alcohol) needed to improve gene expression can be associated with toxicity, inflammation, and other adverse effects in muscle tissues. Block copolymers have been used to improve gene expression in muscle or to modify the physiology of the muscle for subsequent therapeutic applications. See U.S. Pat. Nos. 5,552,309; 5,470,568; 5,605,687; and 5,824,322. For example, block copolymers can be used in a gel-like form (more than 1% of block copolymers) to formulate virus particles used to perform gene transfer in the vasculature. In the same range of block copolymers concentration (1-10%), it is possible with block copolymer to modify the permeability of damaged muscle tissue (radiation and electrical injury, and frost bite). In addition DNA molecules can be incorporated into cells following membrane permeabilization with block copolymers. For these applications, block copolymers were used at concentrations giving gel-like structures and viscous delivery systems. These systems are unlikely to enable diffusion of the DNA injected into the muscle, however, thus limiting infusion of the DNA into the myofibers.

There is thus a need for compositions and methods increasing efficacy of polynucleotides expression upon administration to a patient, in particular, in the muscle and in the skin. There is also a need for methods of increasing the efficiency of delivering polynucleotides to cells.

Beside the need to improve gene expression in muscle and skin, other tissues in the body would benefit from a gene transfer in a situation when there is a genetic disorder, and/or an abnormal over-expression of a gene, and/or absence of a normal gene.

Several polynucleotides such as RNA, DNA, viruses, and ribozymes can be used for gene therapy purposes. However, many problems, like the ones described below, have been encountered for successful gene therapies.

The use of antisense polynucleotides to treat genetic diseases, cell mutations (including cancer causing or enhancing mutations) and viral infections has gained widespread attention. This treatment tool is believed to operate, in one aspect, by binding to "sense" strands of mRNA encoding a protein believed to be involved in causing the disease site sought to be treated, thereby stopping or inhibiting the translation of the mRNA into the unwanted protein. In another aspect, genomic DNA is targeted for binding by the antisense polynucleotide (forming a triple helix), for instance, to inhibit transcription. See Helene, *Anti-Cancer Drug Design*, 6:569 (1991). Once the sequence of the mRNA sought to be bound is known, an antisense molecule can be designed that binds the sense strand by the Watson-Crick base-pairing rules, forming a duplex structure analogous to the DNA double helix. *Gene Regulation: Biology of Antisense RNA and DNA*, Erikson and lxzant, eds., Raven Press, New York, 1991; Helene, *Anti-Cancer Drug Design*, 6:569 (1991); Crooke, *Anti-Cancer Drug Design*, 6:609 (1991). A serious barrier to fully exploiting this technology is the problem of efficiently introducing into cells a sufficient number of antisense molecules to effectively interfere with the translation of the targeted mRNA or the function of DNA.

SUMMARY OF THE INVENTION

The invention relates to compositions for inducing activation of dendritic cells comprising a polynucleotide and at least one block copolymer of an alkylether. Further, the present invention relates to methods of activation of dendritic cells comprising administering, particularly intramuscular and intradermal administration, of polynucleotides, such as viruses, RNA, DNA, plasmid DNA or derivatives thereof, and at least one polyoxyethylene-polyoxypropylene block copolymer. In particular embodiments the block copolymer is present in amounts insufficient for gel formation. The invention also relates to methods of use and compositions comprising at least one polynucleotide or derivative thereof and at least one block copolymer wherein the block copolymer is present at a concentration below about 15% wt/vol. In more particular embodiments, the compositions further comprise a polycation. The compositions also comprise mixtures of block copolymers. The invention also relates to compositions wherein the composition forms a molecular solution or colloidal dispersion, including but not limited to, a suspension, emulsion, microemulsion, micelle, polymer complex, or other types of molecular aggregates. These compositions are useful for increasing the level of production and infiltration for DCs in response to the expression of the gene product encoded by the polynucleotide present in the compositions. The compositions are also useful for increasing the immune response and to generate large amounts of dendritic cells in vivo and in vitro. The invention further relates to methods of delivering polynucleotides to a cell comprising administering to a cell the described compositions.

The invention is based in part, on a number of unanticipated surprising discoveries. One is that the infiltration and activation of dendritic cells in vitro increased significantly upon previous exposure of the cells to a composition comprising a polynucleotide and at least one block copolymer. Another is that immunization is improved when polynucleotide molecules (e.g. plasmid DNA and viruses) are formulated with a single or a combination of block copolymers. The other is that when block copolymers, also called "poloxamers", are used, fewer polynucleotide molecules are required to get an immune response, the time to raise the response is shortened, and that there is no need for a booster injection. As a result, using fewer polynucleotide molecules will decrease the likelihood of getting polynucleotides integrated into the chromosome(s) of the host organism. Further, using fewer polynucleotides will decrease the likelihood of developing anti-polynucleotide (or anti-DNA) antibodies which have been associated with diseases such as, but not limited to, systemic lupus erythematosus.

DETAILED DESCRIPTION OF THE INVENTION

Definitions

As used herein, the terms below have the following meaning:

| Term | Definition |
|---|---|
| Backbone: | Used in graft copolymer nomenclature to describe the chain onto which the graft is formed. |
| Block copolymer: | A combination of two or more chains of constitutionally or configurationally different features. |
| Branched polymer: | A combination of two or more chains linked to each other, in which the end of at least one chain is bonded at some point along the other chain. |
| Chain: | A polymer molecule formed by covalent linking of monomeric units. |
| Configuration: | Organization of atoms along the polymer chain, which can be interconverted only by the breakage and reformation of primary chemical bonds. |
| Conformation: | Arrangements of atoms and substituents of the polymer chain brought about by rotations about single bonds. |
| Copolymer: | A polymer that is derived from more than one species of monomer. |
| Cross-link: | A structure bonding two or more polymer chains together. |
| Dendrimer: | A regularly branched polymer in which branches start from one or more centers. |
| Dispersion: | Particulate matter distributed throughout a continuous medium. |
| Graft copolymer: | A combination of two or more chains of constitutionally or configurationally different features, one of which serves as a backbone main chain, and at least one of which is bonded at some points along the backbone and constitutes a side chain. |
| Homopolymer: | Polymer that is derived from one species of monomer. |
| Link: | A covalent chemical bond between two atoms, including bond between two monomeric units, or between two polymer chains. |
| Polymer blend: | An intimate combination of two or more polymer chains of constitutionally or configurationally different features, which are not bonded to each other. |
| Polymer fragment (or Polymer segment): | A portion of polymer molecule in which the monomeric units have at least one constitutional or configurational feature absent from adjacent portions. |
| Polynucleotide: | A natural or synthetic nucleic acid sequence. |
| Repeating unit: | Monomeric unit linked into a polymer chain. |
| Side chain: | The grafted chain in a graft copolymer. |
| Starblock copolymer: | Three or more chains of different constitutional or configurational features linked together at one end through a central moiety. |
| Star polymer: | Three or more chains linked together at one end through a central moiety. |
| Surfactant: | Surface active agent that is adsorbed at interface. |
| Viral vector: | A construct derived from a virus and used in gene transfer. |

Composition

The present invention is directed to compositions for activation of dendritic cells comprising at least one block copolymer and compositions comprising at least one polynucleotide or derivative therof and at least one polyoxyethylene-polyoxypropylene block copolymer. The present invention is also directed to methods of inducing the activation of dendritic cells and increasing the immune response of an animal by administrating the compositions.

Preferred embodiments include compositions comprising polynucleotides and block copolymers with cationic segments as well as compositions comprising polynucleotides and nonionic polyether block copolymers. In one embodiment, particularly useful for intramuscular and intradermal administration, polynucleotides are formulated with block copolymers of poly(oxyethylene) and poly(oxypropylene). The preferred compositions of this invention further comprise polycations.

The compositions of the current invention provide an efficient vehicle for introducing polynucleotides into a cell, protecting polynucleotides against degradation in body fluids, transport of polynucleotides across biological membranes and biological barriers (such as the blood-brain barrier, blood-cerebral fluid barrier, and intestinal barrier), modification of biodistribution of polynucleotides in the body and enhancement of gene expression including selective gene expression in various tissues and organs in the body of human or animal.

The invention further relates to methods of inserting or delivering polynucleotides into cells utilizing the compositions of the invention, and methods of treatment comprising administering these compositions to humans and animals.

In a preferred embodiment, the block copolymer conforms to one of the following formulae:

wherein A and A' are A-type linear polymeric segments, B and B' are B-type linear polymeric segments, and $R_1$, $R^2$, $R^3$, and $R_4$ are either block copolymers of formulas (I), (II), or (III), or hydrogen and L is a linking group, with the proviso that no more than two of $R_1$, $R_2$, $R_3$, or $R_4$ are hydrogen.

In another preferred embodiment, the block copolymers are poly(oxyethylene) and poly(oxypropylene) chain segments. In yet another preferred embodiment, the polynucleotide compositions have polycationic polymers having a plurality of cationic repeating units. In this case, the polynucleotides can be complexed with the polycation and stabilized in the complex. These compositions demonstrate increased permeability across cell membranes and are well suited for use as vehicles for delivering nucleic acid into cells.

In another embodiment, the invention relates to polynucleotide compositions having:

(a) a polynucleotide or derivative thereof;

(b) a block copolymer having a polyether segment and a polycation segment, wherein the polyether segment comprises at least an A-type block, and the polycation segment comprises a plurality of cationic repeating units.

In a preferred second embodiment, the copolymer relates to polymers of formulae:

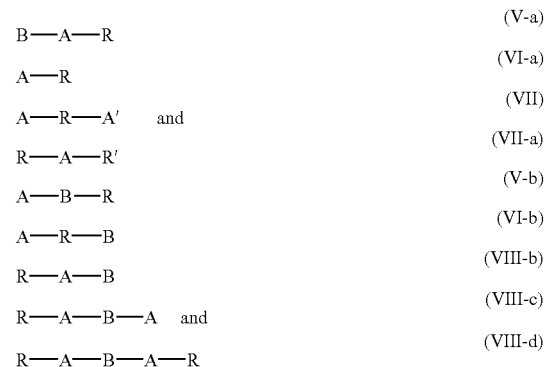

wherein A, A', and B are as described above, wherein R and R' are polymeric segments having a plurality of cationic repeating units, and each cationic repeating unit in a segment is the same or different from another unit in the segment. The polymers of this embodiment can be termed "polynonionic/polycationic" polymers. Preferred polynonionic/polycationic polymers include polycations that are covalently linked to nonionic polymer segments where the nonionic polymer segments are homopolymer or copolymer of at least one of the monomers selected from the group consisting of acrylamide, gycerol, vinylalcohol, vinylpyrrolidone, vinylpyridine, vinylpyridine N-oxide, oxazoline, or a acroylmorpholine, and derivatives thereof. This includes for example polyacrylamides, polygycerols, polyvinylalcohols, polyvinylpyrrolidones, polyvinylpyridine N-oxides, copolymers of vinylpyridine N-oxide and vinylpyridine, polyoxazolines, polyacroylmorpholines or derivatives thereof. Nonionic segments comprising products of polymerization of vinyl monomers are also preferredThe R and R', blocks can be termed "R-type" polymeric segments or blocks. The polynucleotide compositions of this embodiment provide an efficient vehicle for introducing polynucleotides into a cell.

Accordingly, the invention thus further relates to methods of inserting polynucleotide into cells utilizing the compositions of the invention.

In yet another embodiment, the invention relates to polynucleotide compositions comprising a polynucleotide derivative comprising a polynucleotide segment and a polyether segment attached to one or both of the polynucleotide 5' and 3' ends, wherein the polyether comprises an A-type polyether segment.

In a preferred third embodiment, the derivative comprises a block copolymer of formulas:

| Designation | Structure |
| --- | --- |
| IX-a) | A-pN |
| (X-a) | pN-A |
| (XI) | A-pN-A' |
| (XII) | pN-A-B, |
| (XIII) | B-A-pN |
| (XIII-a) | A-B-A-pN |
| (XIII-b) | pN-A-B-A-pN |
| (IX-b) | A-pN-R |

-continued

| Designation | Structure |
|---|---|
| (IX-c) | R-A-pN |
| (IX-d) | A-R-pN |
| (X-b) | pN-A-R |
| (X-c) | R-pN-A |
| (X-d) | pN-R-A |
| (X-e) | B-A-B-pN |
| (X-f) | pN-B-A-B-pN | wherein pN represents a polynucleotide having 5' to 3' orientation, and A, A', and B are polyether segments as described above. In another preferred third embodiment, the polynucleotide complex comprises a polycationic polymer. The polynucleotide component (pN) of formulas (IX) through (XIII) will preferably have from about 5 to about 1,000,000 bases, more preferably about 5 to about 100,000 bases, yet more preferably about 10 to about 10,000 bases.

The polynucleotide compositions provide an efficient vehicle for introducing polynucleotides into a cell. Accordingly, the invention also relates to methods of inserting polynucleotide into cells the compositions of the invention. In another preferred embodiment, polynucleotides are covalently linked to block copolymers of poly(oxyethylene) and poly(oxypropylene).

Another embodiment of the invention relates to a polyetherpolycation copolymers having a polymer, a polyether segment, and a polycationic segment having a plurality of cationic repeating units of formula —NH—$R_0$, wherein $R_0$ is a straight chain aliphatic group of 2 to 6 carbon atoms, which may be substituted, wherein said polyether segments comprise at least one of an A-type of B-type segment. In another preferred embodiment, the polycation polymer has a polymer according to the following formulae:

 B-A-R        (V)

 A-R        (VI)

 A-R-A'        (VII)

and

 R-A-R',        (VIII)

wherein A, A', and B are as described above, wherein R and R' are polymeric segments having a plurality of cationic repeating units of formula —NH—$R_0$—, wherein $R_0$ is a straight chain aliphatic group having from 2 to 6 carbon atoms, which may be substituted. Each —NH—$R^0$— repeating unit in an R-type segment can be the same or different from another —NH—$R^0$— repeating unit in the segment.

In yet another embodiment, the invention provides a polycationic polymer having a plurality of repeating units of formula:

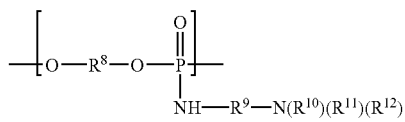

where $R^8$ is:

(1) —$(CH_2)_n$—$CH(R^{13})$—, wherein n is an integer from 0 to about 5, and $R^{13}$ is hydrogen, cycloalkyl having 3-8 carbon atoms, alkyl having 1-6 carbon atoms, or $(CH_2)_m R^{14}$, where m is an integer from 0 to about 12 and $R^{14}$ is a lipophilic substituent of 6 to 20 carbon atoms;

(2) a carbocyclic group having 3-8 ring carbon atoms, wherein the group can be for example, cycloalkyl or aromatic groups, and which can include alkyl having 1-6 carbon atoms, alkoxy having 1-6 carbon atoms, alkylamino having 1-6 carbon atoms, dialkylamino wherein each alkyl independently has 1-6 carbon atoms, amino, sulfonyl, hydroxy, carboxy, fluoro, or chloro substituents; or (3) a heterocyclic group, having 3-8 ring atoms, including heterocycloalkyl or heteroaromatic groups from 1 to 4 heteroatoms selected from the group consisting of oxygen, nitrogen, sulfur and mixtures thereto, and which further can include alkyl having 1-6 carbon atoms, alkoxy having 1-6 carbon atoms, alkylamino having 1-6 carbon atoms, dialkylamino wherein each alkyl independently has 1-6 carbon atoms, amino, sulfonyl, hydroxy, carboxy, fluoro or chloro substituents.

$R^9$ is a straight chain aliphatic group of 1 to 12 carbon atoms, and $R^{10}$, $R^{11}$, and $R^{12}$ are independently hydrogen, an alkyl group of 1-4 carbon atoms. $R^9$ preferably is 2-10 carbon atoms, more preferably, 3-8 carbon atoms. $R^{14}$ preferably includes an intercalating group, which is preferably an acrydine or ethydium bromide group. The number of repeating units in the polymer is preferably between about 3 and 50, more preferably between about 5 and 20. This polymer structure can be incorporated into other embodiments of the invention as an R-type segment or polycationic polymer. The ends of this polymer can further be modified with a lipid substituent.

The monomers that are used to synthesize polymers of this embodiment are suitable for use as the monomers fed to a DNA synthesizer, as described below. Thus, the polymer can be synthesized very specifically. Further, the additional incorporation of polynucleotide sequences, polyether blocks, and lipophilic substituents can be done using the advanced automation developed for polynucleotide syntheses. This embodiment also encompasses the method of synthesizing a polycationic polymer.

In yet another embodiment, the invention relates to polymers having a plurality of covalently bound polymer segments wherein the segments have (a) at least one polycation segment which segment is a cationic homopolymer, copolymer, or block copolymer comprising at least three aminoalkylene monomers, said monomers being selected from the group consisting of: (i) at least one tertiary amino monomer of the formula:

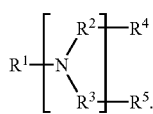        A and the quaternary salts of said tertiary amino monomer, and (ii) at least one secondary amino monomer of the formula:

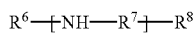        B $R^6$—⁅NH—$R^7$⁆—$R^8$ and the acid addition and quaternary salts of said secondary amino monomer, in which:

$R^1$ is hydrogen, alkyl of 2 to 8 carbon atoms, an A monomer, or a B monomer; each of $R^2$ and $R^3$, taken independently of the other, is the same or different straight or branched chain alkanediyl group of the formula:

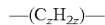

in which z has a value of from 2 to 8; $R^4$ is hydrogen satisfying one bond of the depicted geminally bonded carbon atom; and $R^5$ is hydrogen, alkyl of 2 to 8 carbon atoms, an A monomer, or a B monomer; $R^6$ is hydrogen, alkyl of 2 to 8 carbon atoms, an A monomer, or a B monomer; $R^7$ is a straight or branched chain alkanediyl group of the formula:

in which z has a value of from 2 to 8; and $R^8$ is hydrogen, alkyl of 2 to 8 carbon atoms, an A monomer, or a B monomer; and (b) at least one straight or branched chained polyether segment having from about 5 to about 400 monomeric units which is:
  (i) a homopolymer of a first alkyleneoxy monomer —$OC_nH_{2n}$— or
  (ii) a copolymer or block copolymer of said first alkyleneoxy monomer and a second different alkyleneoxy monomer —$OC_mH_{2m}$—, in which n has a value of 2 or 3 and m has a value of from 2 to 4.

Polymers of formulas (I), (II), (III), or (IV) can also be mixed with each other or can be mixed either additionally or alternatively with one or more of the polymers of formula (V-a or b), (VI-a or b), (VII-a or b), and (VIII-a or b) and/or with polynucleotide derivatives of formulas (IX-a, b, c, or d), (X-a, b, c, d, e, or f), (XI), (XII) or (XIII) to provide an efficient vehicle for delivering polynucleotide to the interior of cells.

The degree of polymerization of the hydrophilic (A-type) blocks or the hydrophobic (B-type) blocks of formulas (I)-(XIII) can preferably be between about 5 and about 400. More preferably, the degree of polymerization shall be between about 5 and about 200, still more preferably, between about 5 and about 80. The degree of polymerization of the R-type polycation blocks can preferably be between about 2 and about 300. More preferably, the degree of polymerization shall be between about 5 and about 180, still more preferably, between about 5 and about 60. The degree of polymerization of the polycationic polymer can preferably be between about 10 and about 10,000. More preferably, the degree of polymerization shall be between about 10 and about 1,000, still more preferably, between about 10 and about 100.

The repeating units that comprise the blocks, for A-type, B-type and R-type blocks, will generally have molecular weight between about 30 and about 500, preferably between about 30 and about 100, still more preferably between about 30 and about 60. Generally, in each of the A-type or B-type blocks, at least about 80% of the linkages between repeating units will be ether linkages, preferably, at least about 90% will be ether linkages, more preferably, at least about 95% will be ether linkages. Ether linkages, for the purposes of this application, encompass glycosidic linkages (i.e., sugar linkages). However, in one aspect, simple ether linkages are preferred.

In yet another preferred embodiment, the compositions of the invention are useful for gene therapy purposes, including gene replacement or excision therapy, and gene addition therapy, vaccination, and any therapeutic situation in which a polypeptide should be expressed or down-regulated in the body or in vitro. In one aspect of this invention the polynucleotide compositions are used for gene therapy in muscle tissue, including but not limited to smooth, skeletal and cardiac muscles of the human or animals. It is preferred that compositions for intramuscular administration comprise the block copolymers of poly(oxyethylene) and poly(oxypropylene).

In still another preferred embodiment, the invention relates to compositions comprising at least one poly(oxyethylene) and poly(oxypropylene) block copolymer with oxyethylene content of 50% or less, and at least one poly(oxyethylene) and poly(oxypropylene) block copolymer with oxyethylene content of 50% or more, and a polynucleotide. The preferable ratio by weight of the block copolymer with oxyethylene content of 50% or less to the block copolymer with oxyethylene content of 50% or more is 1:2, more preferably 1:5.

It is preferred that the compositions of this invention do not form gels. It is preferred that the compositions form molecular solutions or colloidal dispersions. The colloidal dispersions include suspensions, emulsions, microemulsions, micelles, polymer complexes, or other types of molecular aggregates are particularly preferred. In one aspect the concentration of the polymers and block copolymers in the polynucleotide compositions is less that 10%, preferably less that 1%, more preferred less than 0.5%, yet more preferred less than 0.1%.

Block copolymers are most simply defined as conjugates of at least two different polymer segments (Tirrel, M., *Interactions of Surfactants with Polymers and Proteins*, Goddard E. D. and Ananthapadmanabhan, K. P. (eds.), CRC Press, Boca Raton, Ann Arbor, London, pp. 59-122, (1992). The simplest block copolymer architecture contains two segments joined at their termini to give an A-B type diblock. Consequent conjugation of more than two segments by their termini yields an A-B-A type triblock, A-B-A-B-type multiblock, or even multisegment A-B-C-architectures. If a main chain in the block copolymer can be defined in which one or several repeating units are linked to different polymer segments, then the copolymer has a graft architecture of, e.g., an $A(B)_n$ type. More complex architectures include for example $(AB)_n$ or $A_nB_m$ starblocks which have more than two polymer segments linked to a single center. Formulas XVIII-XXIII of the invention are diblocks and triblocks. At the same time, conjugation of polycation segments to the ends of polyether of formula XVII yields starblocks (e.g., $(ABC)_4$ type). In addition, the polyspermine of examples 13-15 (below) are branched. Modification of such a polycation with poly(ethylene oxide) yields a mixture of grafted block copolymers and starblocks. In accordance with the present invention, all of these architectures can be useful for polynucleotide delivery.

The entire disclosure of U.S. Pat. No. 5,783,178 is hereby incorporated herein by reference.

In another aspect, the invention provides a polynucleotide complex between a polynucleotide and polyether block copolymers. Preferably, the polynucleotide complex will further include a polycationic polymer. The compositions can further include suitable targeting molecules and surfactants. In another aspect, the invention provides a polynucleotide complex between a polynucleotide and a block copolymer comprising a polyether block and a polycation block. In yet another aspect, the invention provides polynucleotides that have been covalently modified at their 5' or 3' end to attach a polyether polymer segment.

Polycations. Preferred polycation polymers and polycation segments of the copolymers include but are not limited to polyamines (e.g., spermine, polyspermine, polyethyleneimine, polypropyleneimine, polybutylene-imine, polypentyleneimine, polyhexyleneimine and copolymers thereof), copolymers of tertiary amines and secondary amines, partially or completely quaternized amines, polyvinyl pyridine, and the quaternary ammonium salts of these polycation segments. These preferred polycation fragments also include aliphatic, heterocyclic or aromatic ionenes. Rembaum et al., *Polymer Letters*, 6:159 (1968); Tsutsui, T., *Development in Ionic Polymers*-2, Wilson A. D. and Prosser, H. J. (Eds.) Applied Science Publishers, London, New York, Vol. 2, pp. 167-187 (1986).

The polycationic polymers and the R-type blocks have several positively ionizable groups and a net positive charge at physiologic pH. The polyether/polycation polymers of Formulas (V)-(VIII) can also serve as polycationic polymers. Preferably, the polycation segments have at least about 3 positive charges at physiologic pH, more preferably, at least about 6, still more preferably, at least about 12. Also preferred are polymers or segments that, at physiologic pH, can present positive charges with a distance between the charges of about 2 Å to about 10 Å. The distances established by ethyleneimine, aminopropylene, aminobutylene, aminopentylene and aminohexylene repeating units, or by mixtures of at least two of these groups are most preferred. Preferred are polycationic segments that utilize ($NCH_2CH_2$), ($NCH_2CH_2CH_2$), ($NCH_2CH_2CH_2CH_2$), ($NCH_2CH_2CH_2CH_2CH_2$), and ($NCH_2CH_2CH_2CH_2CH_2CH_2$) repeating units, or a mixture thereof.

In preferred compositions of the current invention the polycation polymers and polyether/polycation copolymers are mixed with polyoxyethylene-polyoxypropylene block copolymers. Oligoamines and conjugates of oligoamines with polyethers, including conjugates of oligoamines with polyoxyethylene-polyoxypropylene block copolymers can be used in this invention as polycationic molecules, particularly, in mixtures with polyoxyethylene-polyoxypropylene block copolymers. Examples of oligoamines useful in this invention include but are not limited to spermine, spermidine, and other DNA-condensing agents. Ethyleneimine oligoamines such as diethylenetriamine and pentaethylenehexamine, propyleneimine oligoamines such as N-(3-aminopropyl)-1,3-propanediamine and N,N'-bis-(3-aminopropyl)-1,3-propanediamine, butyleneimine oligoamines, pentyleneimine oligoamines, hexyleneimine oligoamines, heptyleneimine oligoamines and derivatives thereof are particularly useful in this invention.

Polycation segments having an —N—$R^0$— repeating unit are also preferred. $R^0$ is preferably an ethylene, propylene, butylene, pentylene, or hexylene chain which can be modified. In a preferred embodiment, in at least one of the repeating units $R^0$ includes a DNA intercalating group such as an ethidium bromide group. Such intercalating groups can increase the affinity of the polymer for nucleic acid. Preferred substitutions on $R^0$ include alkyl of 1-6 carbon atoms, hydroxy, hydroxyalkyl, wherein the alkyl has 1-6 carbon atoms, alkoxy having 1-6 carbon atoms, an alkyl carbonyl group having 2-7 carbon atoms, alkoxycarbonyl wherein the alkoxy has 1-6 carbon atoms, alkoxycarbonylalkyl wherein the alkoxy and alkyl each independently has 1-6 carbon atoms, alkylcarboxyalkyl wherein each alkyl group has 1-6 carbon atoms, aminoalkyl wherein the alkyl group has 1-6 carbon atoms, alkylamino or dialkylamino where each alkyl group independently has 1-6 carbon atoms, mono- or dialkylaminoalkyl wherein each alkyl independently has 1-6 carbon atoms, chloro, or chloroalkyl wherein the alkyl has from 1-6 carbon atoms, fluoro, or fluoroalkyl wherein the alkyl has from 1-6 carbon atoms, cyano, or cyano alkyl wherein the alkyl has from 1-6 carbon atoms or a carboxyl group. More preferably, $R^0$ is ethylene, propylene, or butylene.

The polycation polymers and polycation segments in the copolymers of the invention can be branched. For example, polyspermine-based copolymers are branched. The cationic segment of these copolymers was synthesized by condensation of 1,4-dibromobutane and N-(3-aminopropyl)-1,3-propanediamine. This reaction yields highly branched polymer products with primary, secondary, and tertiary amines.

An example of branched polycations are products of the condensation reactions between polyamines containing at least 2 nitrogen atoms and alkyl halides containing at least 2 halide atoms (including bromide or chloride). In particular, the branched polycations are produced as a result of polycondensation. An example of this reaction is the reaction between N-(3-aminopropyl)-1,3-propanediamine and 1,4-dibromobutane, producing polyspermine. Branched polycation polymers of this type can be represented by the formula:

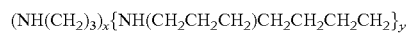

Another example of a branched polycation is polyethyleneimine represented by the formula:

Additionally, cationic dendrimers, for example, polyamidoamines can be also used as polycation segments of block copolymers for gene delivery. Tomalia et al., *Angew. Chem., Int. Ed. Engl.*, 29, 138 (1990).

In a preferred embodiment the polycations are covalently linked with nonionic polymer segments. It is preferred that nonionic polymer segments comprise water-soluble polymers that are nontoxic and nonimmunogenic. One preferred example of such polymers is polyether polymers that are homopolymers and copolymers of the ethyleneoxy monomer (—$OCH_2CH_2$—) and propyleneoxy monomer (—$OCH(CH_3)CH_2$—) including poly(oxyethylene), poly(oxypropylene), poly(oxyethylene)/poly(oxypropylene) block copolymers and poly(oxyethylene)/poly(oxypropylene) random copolymers. Another preferred example of nonionic polymer segment of use in the present invention is homopolymer or copolymer of at least one of the monomers selected from the group consisting of acrylamide, gycerol, vinylalcohol, vinylpyrrolidone, vinylpyridine, vinylpyridine N-oxide, oxazoline, or a acroylmorpholine, and derivatives thereof. This includes for example polyacrylamides, polygycerols, polyvinylalcohols, polyvinylpyrrolidones, polyvinylpyridine N-oxides, copolymers of vinylpyridine N-oxide and vinylpyridine, polyoxazolines, polyacroylmorpholines or derivatives thereof. Nonionic segments comprising products of polymerization of vinyl monomers are also preferred, including but not limiting to the following nonionic polymer segments and derivatives thereof:

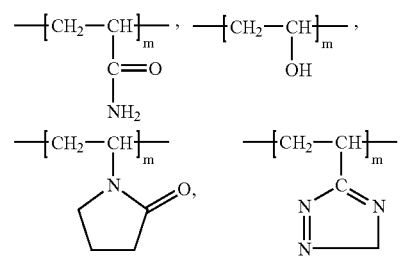

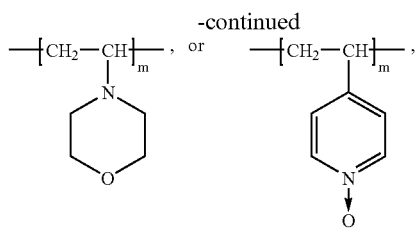

in which m a value 3 to about 10,000.

Examples of useful polymers pursuant to formulas (V)-(VIII) include the poly(oxyethylene)-poly-L-lysine) diblock copolymer of the following formula:

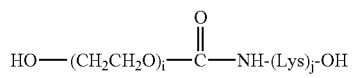

wherein i is an integer of from about 5 to about 100, and j is an integer from about 4 to about 100.

A second example is the poly(oxyethylene)-poly-(L-alanine-L-lysine) diblock
copolymer of formula:

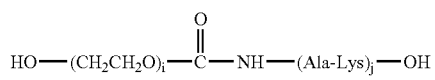
(XIX)

wherein i is an integer of from about 5 to about 100, and j is an integer from about 4 about 100.

A third example is the poly(oxyethylene)-poly(propyleneimine/butyleneimine) diblock copolymer of the following formula:

(XX)

wherein i is an integer from about 5 about 200 and j is an integer from 1 to about 10.

A fourth example is the poly(oxyethylene)-poly(N-ethyl-4-vinylpyridinium bromide) ("pOE-pEVP-Br") of formula:

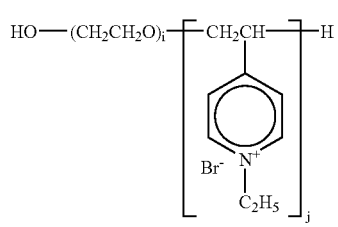
(XXI)

wherein i is an integer of from about 5 to about 100 and j is an integer of from about 10 to about 500. Still another example is the polymer of formula:

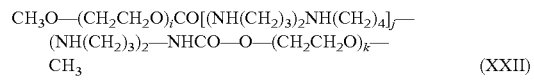
(XXII)

wherein i is an integer from about 10 to about 200, j is an integer from about 1 to about 8, and k is an integer from about 10 to about 200. Still another example is the polymer of formula:

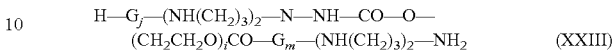
(XXIII)

wherein "G" comprises —(NH(CH$_2$)$_3$)$_3$—CH$_2$NH$_2$—, $_i$ and $_j$ are as defined for formula (XVIII), and $_m$ is an integer from about 1 to about 8.

Nonionic polyether block copolymers and polyether segments are exemplified by the block copolymers having the formulas:

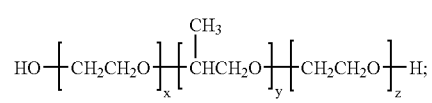
(XXIV)

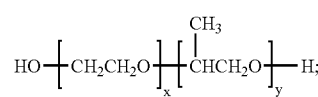
(XXV)

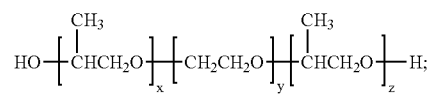
(XXVI)

-continued

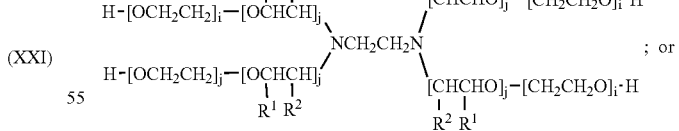
(XXVII)

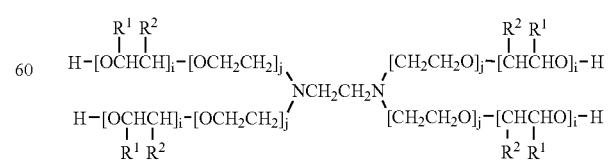
(XXVIII)

in which x, y, z, i, and j have values from about 2 to about 800, preferably from about 5 to about 200, more preferably from about 5 to about 80, and wherein for each $R_1$, $R_2$ pair, one is hydrogen and the other is a methyl group. Formulas (XXIV) through (XXVI) are oversimplified in that, in practice, the orientation of the isopropylene radicals within the B block will be random. This random orientation is indicated in formulas (XXVII) and (XXVIII), which are more complete. Such poly(oxyethylene)-poly(oxypropylene) block copolymers have been described by Santon, *Am. Perfumer Cosmet.*, 72(4):54-58 (1958); Schmolka, Loc. cit. 82(7):25-30 (1967); *Non-ionic Surfactants*, Schick, ed. (Dekker, N.Y., 1967), pp. 300-371. A number of such compounds are commercially available under such generic trade names as "lipoloxamers", "poloxamers", "Pluronic®", and "synperonics."poly(oxyethylene)-poly(oxypropylene) polymers within the B-A-B formula are often referred to as "reversed" Pluronic, "Pluronic-R®" or "meroxapol."

The "polyoxamine" polymer of formula (XXVII) is available from BASF (Wyandotte, Mich.) under the tradename Tetronic®. The order of the polyoxyethylene and polyoxypropylene blocks represented in formula (XXVII) can be reversed, creating Tetronic-R®, of formula (XXVIII) also available from BASF. See, Schmolka, *J. Am. Oil. Soc.*, 59:110 (1979). Polyoxypropylene-polyoxyethylene block copolymers can also be designed with hydrophilic blocks comprising a random mix of ethylene oxide and propylene oxide repeating units. To maintain the hydrophilic character of the block, ethylene oxide will predominate. Similarly, the hydrophobic block can be a mixture of ethylene oxide and propylene oxide repeating units. Such block copolymers are available from BASF under the tradename Pluradot™.

A number of pluronics are designed to meet the following formula:

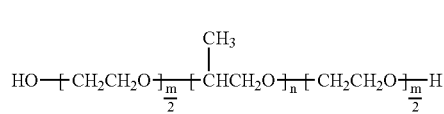

(XXIX)

The values of m and n will usually represent a statistical average and the number of repeating units of the first block of a given molecule will generally not be exactly the number of repeating units of the third block. The characteristics of a number of block copolymers, described with reference to formula (XXIX), are as follows:

| Copolymer | MW | Average # of oxypropylene units, n | Average # of oxyethylene units, n | HLB | CMC, μM$^c$ |
|---|---|---|---|---|---|
| L31 | 1100 | 17.1 | 2.5 | 5 | 1180 |
| L35 | 1900 | 16.4 | 21.6 | 19 | 5260 |
| L43 | 1850 | 22.3 | 12.6 | 12 | 2160 |
| L44 | 2200 | 22.8 | 20.0 | 16 | 3590 |
| L61 | 2000 | 31.0 | 4.5 | 3 | 110 |
| L62 | 2500 | 34.5 | 11.4 | 7 | 400 |
| L64 | 2900 | 30.0 | 26.4 | 15 | 480 |
| F68 | 8400 | 29.0 | 152.7 | 29 | 480 |
| L81 | 2750 | 42.7 | 6.2 | 2 | 23 |
| P84 | 4200 | 43.4 | 38.2 | 14 | 71 |
| P85 | 4600 | 39.7 | 52.3 | 16 | 65 |
| F87 | 7700 | 39.8 | 122.5 | 24 | 91 |
| F88 | 11400 | 39.3 | 207.8 | 28 | 250 |
| L92 | 3650 | 50.3 | 16.6 | 6 | 88 |
| F98 | 13000 | 44.8 | 236.4 | 28 | 77 |
| L101 | 3800 | 58.9 | 8.6 | 1 | 2.1 |
| P103 | 4950 | 59.7 | 33.8 | 9 | 6.1 |
| P104 | 5900 | 61.0 | 53.6 | 13 | 3.4 |
| P105 | 6500 | 56.0 | 73.9 | 15 | 6.2 |
| F108 | 14600 | 50.3 | 265.4 | 27 | 22 |
| L121 | 4400 | 68.2 | 10.0 | 1 | 1 |
| P123 | 5750 | 69.4 | 39.2 | 8 | 4.4 |
| F127 | 12600 | 65.2 | 200.4 | 22 | 2.8 |

The average numbers of oxyethylene and oxypropylene units were calculated using the average molecular weighs (MW) provided by the manufacturer. The hydrophilic-lipophilic balance (HLB) of the copolymers were determined by the manufacturer (BASF Co.). The critical micellization concentrations (CMC) were determined by the surface tension method described in Kabanov et al., *Macromolecules* 28: 2303-2314 (1995).

Some other specific poly(oxyethylene)-poly(oxypropylene) block copolymers relevant to the invention include:

| No. | Block Copolymer | Formula | Hydrophobe Weight | Hydrophobe Percentage |
|---|---|---|---|---|
| 1 | F38 | XXIV | 900 | 20% |
| 2 | L42 | XXIV | 1200 | 80% |
| 3 | L63 | XXIV | 1750 | 70% |
| 4 | P65 | XXIV | 1750 | 50% |
| 5 | L72 | XXIV | 2050 | 80% |
| 6 | F75 | XXIV | 2050 | 50% |
| 7 | P77 | XXIV | 2050 | 30% |
| 8 | L122 | XXIV | 4000 | 80% |
| 9 | 10R5 | XXVI | 1000 | 50% |
| 10 | 10R8 | XXVI | 1000 | 20% |
| 11 | 12R3 | XXVI | 1200 | 70% |
| 12 | 17R1 | XXVI | 1700 | 90% |
| 13 | 17R2 | XXVI | 1700 | 80% |
| 14 | 17R4 | XXVI | 1700 | 60% |
| 15 | 17R8 | XXVI | 1700 | 20% |
| 16 | 22R4 | XXVI | 2200 | 60% |
| 17 | 25R1 | XXVI | 2500 | 90% |
| 18 | 25R2 | XXVI | 2500 | 80% |
| 19 | 25R4 | XXVI | 2500 | 60% |
| 20 | 25R5 | XXVI | 2500 | 50% |
| 21 | 25R8 | XXVI | 2500 | 50% |
| 22 | 31R1 | XXVI | 3100 | 90% |
| 23 | 31R2 | XXVI | 3100 | 80% |
| 24 | 31R4 | XXVI | 3100 | 60% |
| 25 | 304 | XXVII | 500 | 60% |
| 26 | 504 | XXVII | 1100 | 60% |
| 27 | 701 | XXVII | 2200 | 90% |
| 28 | 702 | XXVII | 2200 | 80% |
| 29 | 704 | XXVII | 2200 | 60% |
| 30 | 707 | XXVII | 2200 | 30% |
| 31 | 901 | XXVII | 3300 | 90% |
| 32 | 904 | XXVII | 3300 | 60% |
| 33 | 908 | XXVII | 3300 | 20% |
| 34 | 1101 | XXVII | 4400 | 90% |
| 35 | 1102 | XXVII | 4400 | 80% |
| 36 | 1104 | XXVII | 4400 | 60% |
| 37 | 1107 | XXVII | 4400 | 30% |
| 38 | 1301 | XXVII | 5500 | 90% |
| 39 | 1302 | XXVII | 5500 | 80% |
| 40 | 1304 | XXVII | 5500 | 60% |
| 41 | 1307 | XXVII | 5500 | 30% |
| 42 | 1501 | XXVII | 7000 | 90% |
| 43 | 1502 | XXVII | 7000 | 80% |
| 44 | 1504 | XXVII | 7000 | 60% |
| 45 | 1508 | XXVII | 7000 | 20% |
| 46 | 50R1 | XXVIII | 2100 | 90% |

-continued

| No. | Block Copolymer | Formula | Hydrophobe Weight | Hydrophobe Percentage |
|---|---|---|---|---|
| 47 | 50R4 | XXVIII | 2100 | 60% |
| 48 | 50R8 | XXVIII | 2100 | 20% |
| 49 | 70R1 | XXVIII | 3000 | 90% |
| 50 | 70R2 | XXVIII | 3000 | 80% |
| 51 | 70R4 | XXVIII | 3000 | 60% |
| 52 | 90R1 | XXVIII | 3900 | 90% |
| 53 | 90R4 | XXVIII | 3900 | 60% |
| 54 | 90R8 | XXVIII | 3900 | 20% |
| 55 | 110R1 | XXVIII | 4800 | 90% |
| 56 | 110R2 | XXVIII | 4800 | 80% |
| 57 | 110R7 | XXVIII | 4800 | 30% |
| 58 | 130R1 | XXVIII | 5700 | 90% |
| 59 | 130R2 | XXVIII | 5700 | 80% |
| 60 | 150R1 | XXVIII | 6700 | 90% |
| 61 | 150R4 | XXVIII | 6700 | 60% |
| 62 | 150R8 | XXVIII | 6700 | 20% |

In a preferred embodiment, the compositions comprising a polynucleotide or derivative thereof and at least one block copolymer wherein the block copolymer is PLURONIC® F127 and L61. In another embodiment, the composition comprises a polynucleotide and at least one block copolymer, wherein the block copolymer is PLURONIC® P85.

The diamine-linked block copolymer of formula (XXVII) can also be a member of the family of diamine-linked polyoxyethylene-polyoxypropylene polymers of formula:

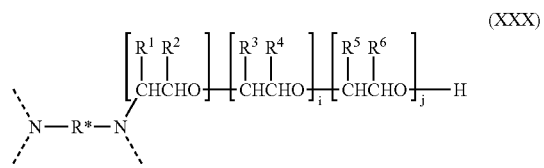

(XXX)

wherein the dashed lines represent symmetrical copies of the polyether extending off the second nitrogen, R* an alkylene of about 2 to about 6 carbons, a cycloalkylene of about 5 to about 8 carbons or phenylene, for $R^1$ and $R^2$, either (a) both are hydrogen or (b) one is hydrogen and the other is methyl, for $R^3$ and $R^4$ either (a) both are hydrogen or (b) one is hydrogen and the other is methyl, if both of $R^3$ and $R^4$ are hydrogen, then one $R^5$ and $R^6$ is hydrogen and the other is methyl, and if one of $R^3$ and $R^4$ is methyl, then both of $R^5$ and $R^6$ are hydrogen.

The hydrophobic/hydrophilic properties of a given block copolymer depends upon the ratio of the number of oxypropylene groups to the number of oxypropylene groups. For a composition containing a single block copolymer of poly(oxyethylene)-poly(oxypropylene), for example, this relationship, taking into account the molecular masses of the central hydrophobic block and the terminal hydrophilic blocks, can be expressed as follows:

$$n = \frac{H}{L} \cdot 1.32$$

in which H is the number of oxypropylene units and L is the number of oxyethylene units. In the general case of a block copolymer containing hydrophobic B-type segments and hydrophilic A-type segments, the hydrophobic-hydrophilic properties and micelle-forming properties are related to the value n as defined as:

$$n = (|B|/|A|) \times (b/a)$$

where |B| and |A| are the number of repeating units in the hydrophobic and hydrophilic blocks of the copolymer, respectively, and b and a are the molecular weights for the respective repeating units.

Selecting a block copolymer with the appropriate n value will depend upon the hydrophobic/hydrophilic properties of the specific agent, or the composite hydrophilic/hydrophilic properties of a mixture of agents to be formulated. Typically, n will range in value from about 0.2 to about 9.0, more preferably between about 0.25 and about 1.5. This range should be viewed not as numerically critical but as expressing the optimum hydrophobic/hydrophilic balance between the predominantly hydrophilic poly(oxyethylene) blocks, and the predominantly hydrophobic poly(oxypropylene) blocks.

An important aspect of the present invention-involves utilizing mixture of different block-copolymers of poly(oxyethylene)-poly(oxypropylene) to achieve a more specific hydrophobic-hydrophilic balance suitable for a given cytokine or mixture of several cytokines, preserving the optimal size of particles. For example, a first block copolymer may have an n of 1.0 whereas a second may have a value of 1.5. If material having an n of 1.3 is desired, a mixture of one weight portion of the first block copolymer and 1.5 weight portion of the second block-copolymer can be employed.

Thus, a more generalized relationship for such mixtures can be expressed as follows:

$$N = 1.32 \cdot \left[ \frac{H_1 \cdot m_1}{(L_1) \cdot (m_1 + m_2)} + \frac{H_2 \cdot m_2}{(L_2) \cdot (m_1 + m_2)} \right]$$

in which $H_1$ and $H_2$ are the number of oxypropylene units in the first and second block copolymers, respectively; $L_1$ is the number of oxyethylene units in the first block copolymer; $L_2$ is the number of oxyethylene units in the second block copolymer; $m_1$ is the weight proportion in the first block-copolymer; and $m_2$ is the weight proportion in the second block copolymer. Typically, N will range in value from about 0.2 to about 9.0, more preferably between about 0.25 and about 1.5.

An even more general case of a mixture of K block copolymers containing hydrophobic B-type block copolymers and hydrophilic A-type block copolymers, the N value can be expressed as follows:

$$N = \frac{b}{a} \sum_{i=1}^{k} \left[ \frac{|B|_i}{|A|_i} \cdot \frac{m_i}{M} \right]$$

where $|A|_i$ and $|B|_i$ are the numbers of repeating units in the hydrophilic (A-type) and hydrophobic (B-type) blocks of the i-th block copolymer, m is the weight proportion of this block copolymers, M is the sum of weight proportions of all block copolymers in the mixture $$\left(M = \sum_{i=1}^{k} m_i\right),$$

and a and b are the molecular weights for the repeating units of the hydrophilic and hydrophobic blocks of these block copolymers respectively.

If only one block copolymer of poly(oxyethylene)-poly(oxypropylene) is utilized, N will equal n. An analogous relationship will apply to compositions employing more than two block copolymers of poly(oxyethylene)-poly(oxypropylene).

Where mixtures of block copolymers are used, a value N will be used, which value will be the weighted average of n for each contributing copolymers, with the averaging based on the weight portions of the component copolymers. The value N can be used to estimate the micelle-forming properties of a mixture of copolymers. The use of the mixtures of block copolymers enhances solubility and prevents aggregation of more hydrophobic block copolymers in the presence of the serum proteins. Particularly, the mixtures comprise poly(oxyethylene)-poly(oxypropylene) block copolymers with the ethylene oxide content of more than 50% solubilize hydrophobic block copolymers with ethylene oxide content of no more than 50%. Preferably, the mixtures of block copolymers comprise block copolymers with oxyethylene content of 70% or more and at least one block copolymer with oxyethylene content of 50% or less. More particularly PLURONIC® F127 is preferred. In such mixtures, the preferred ratio of the hydrophilic and hydrophobic copolymer is at least 2:1 (w/w), preferably at least 5:1 (w/w), still more preferably at least 8:1 (w/w). When copolymers other than polyethylene oxide-polypropylene oxide copolymers are used, similar approaches can be developed to relate the hydrophobic/hydrophilic properties of one member of the class of polymers to the properties of another member of the class.

Using the above parameters, one or more block copolymers of poly(oxyethylene)-poly(oxypropylene) are combined so as to have a value for N of from about 0.1 to about 9, more preferably from about 0.25 to about 1.5. The combined copolymers form micelles, the value of N affecting in part the size of the micelles thus produced. Typically, the micelles will have an average diameter of from about 10 to about 25 nm, although this range can vary widely. The average diameter of any given preparation can be readily determined by quasi-elastic light scattering techniques.

According to one embodiment of the present invention, the compositions comprises a polynucleotide or derivative thereof and at least one polyethylene-polypropylene block copolymer wherein the block copolymers form a molecular solution or colloidal dispersion (the colloidal dispersion includes, but is not limited to, a suspension, emulsion, microemulsion, micelles, polymer complexes, or other types of molecular aggregates or species). In the molecular solution or colloidal dispersion, the size of the molecular species formed by the block copolymers is one major parameter determining usefulness of the compositions of the current invention. After administration in the body large particles are eliminated by the reticuloendothelial system and cannot be easily transported to the disease site (see, for example, Kabanov et al., *J. Contr. Release,* 22, 141 (1992); Volkheimer. *Pathologe* 14:247 (1993); Kwon and Kataoka, *Adv. Drug. Del. Rev.* 16:295 (1995). Also, the transport of large particles in the cell and intracellular delivery is limited or insignificant. See, e.g., Labhasetwar et al. *Adv. Drug Del. Res.* 24:63 (1997). It was demonstrated that aggregated cationic species with a size from 300 nm to over 1 μm are ineffective in cell transfection, see Kabanov et al., *Self-Assembling Complexes for Gene Delivery. From Laboratory to Clinical Trial,* Kabanov et al. (eds.), John Wiley, Chichester (1998) and references cited. Large particles, particularly, those positively charged exhibit high toxicity in the body, in part due to adverse effects on liver and embolism. See e.g., Volkheimer, *Pathologe* 14:247 (1993); Khopade et al., *Pharmazie* 51:558 (1996); Yamashita et al., *Vet Hum. Toxicol.,* 39:71 (1997). Small polymer species are nontoxic, can enter into small capillaries in the body, transport in the body to a disease site, cross biological barriers (including but not limited to the blood-brain barrier and intestinal epithelium), absorb into cell endocytic vesicles, cross cell membranes and transport to the target site inside the cell. The particles in that size range are believed to be more efficiently transferred across the arterial wall compared to larger size microparticles, see Labhasetwar et al., *Adv. Drug Del. Res.* 24:63 (1997). Without wishing to be bound by any particular theory it is also believed that because of high surface to volume ratio, the small size is essential for successful targeting of such particles using targeting molecules. The preferred range of the species formed in the compositions of the current invention is less than about 300 nm, more preferred less than about 100 nm, still more preferred less than about 50 nm.

In another aspect, the invention relates to a polynucleotide complex comprising a block copolymer at least one of formulas (I)-(XIII), wherein the A-type and B-type blocks are substantially made up of repeating units of formula —O—$R^9$, where $R^9$ is:

(1) —$(CH_2)_n$—$CH(R^6)$, wherein n is an integer from 0 to about 5 and $R^6$ is hydrogen, cycloalkyl having 3-8 carbon atoms, alkyl having 1-6 carbon atoms, phenyl, alkylphenyl wherein the alkyl has 1-6 carbon atoms, hydroxy, hydroxyalkyl, wherein the alkyl has 1-6 carbon atoms, alkoxy having 1-6 carbon atoms, an alkyl carbonyl group having 2-7 carbon atoms, alkoxycarbonyl, wherein the alkoxy has 1-6 carbon atoms, alkoxycarbonylalkyl, wherein the alkoxy and alkyl each independently has 1-6 carbon atoms, alkylcarboxyalkyl, wherein each alkyl group has 1-6 carbon atoms, aminoalkyl wherein the alkyl group has 1-6 carbon atoms, alkylamine or dialkylamino, wherein each alkyl independently has 1-6 carbon atoms, mono- or di-alkylaminoalkyl wherein each alkyl independently has 1-6 carbon atoms, chloro, or chloroalkyl wherein the alkyl has from 1-6 carbon atoms, fluoro, fluoroalkyl wherein the alkyl has from 1-6 carbon atoms, cyano or cyano alkyl wherein the alkyl has from 1-6 carbon atoms or carboxyl; (2) a carbocyclic group having 3-8 ring carbon atoms, wherein the group can be for example, cycloalkyl or aromatic groups, and which can include alkyl having 1-6 carbon atoms, alkoxy having 1-6 carbon atoms, alkylamino having 1-6 carbon atoms, dialkylamino wherein each alkyl independently has 1-6 carbon atoms, amino, sulfonyl, hydroxy, carboxy, fluoro or chloro substitutions, or (3) a heterocyclic group, having 3-8 ring atoms, which can include heterocycloalkyl or heteroaromatic groups, which can include from 1-4 heteroatoms selected from the group consisting of oxygen, nitrogen, sulfur, and mixtures thereof, and which can include alkyl of 1-6 carbon atoms, alkoxy having 1-6 carbon atoms, alkylamino having 1-6 carbon atoms, dialkylamino wherein each alkyl independently has 1-6 carbon atoms, amino, sulfonyl, hydroxy, carboxy, fluoro, or chloro substitutions.

Preferably, n is an integer from 1 to 3. The carbocyclic or heterocyclic groups comprising $R^5$ preferably have from 4-7 ring atoms, more preferably 5-6. Heterocycles preferably include from 1-2 heteroatoms, more preferably, the heterocycles have one heteroatom. Preferably, the heterocycle is a carbohydrate or carbohydrate analog. Those of ordinary skill will recognize that the monomers required to make these polymers are synthetically available. In some cases, polymerization of the monomers will require the use of suitable protective groups, as will be recognized by those of ordinary skill in the art. Generally, the A- and B-type blocks are at least about 80% comprised of —$OR^5$— repeating units, more preferably at least about 90%, yet more preferably at least about 95%.

In another aspect, the invention relates to a polynucleotide complex comprising a block copolymer of one of formulas (I)-(XIII) wherein the A-type and B-type blocks consist essentially of repeating units of formula —O—$R^5$ wherein $R^7$ is a C to C alkyl group.

The block copolymers utilized in the invention will typically, under certain circumstances, form micelles of from about 10 nm to about 100 nm in diameter. Micelles are supramolecular complexes of certain amphiphilic molecules that form in aqueous solutions due to microphase separation of the nonpolar portions of the amphiphiles. Micelles form when the concentration of the amphiphile reaches, for a given temperature, a critical micellar concentration ("CMC") that is characteristic of the amphiphile. Such micelles will generally include from about 10 to about 300 block copolymers. By varying the sizes of the hydrophilic and hydrophobic portions of the block copolymers, the tendency of the copolymers to form micelles at physiological conditions can be varied. The micelles have a dense core formed by the water insoluble repeating units of the B blocks and charge-neutralized nucleic acids, and a hydrophilic shell formed by the A blocks. The micelles have translational and rotational freedom in solution, and solutions containing the micelles have low viscosity similar to water. Micelle formation typically occurs at copolymer concentrations from about 0.001 to 5% (w/v). Generally, the concentration of polycationic polymers and polynucleic acid will be less than the concentration of copolymers in the polynucleotide compositions, preferably at least about 10-fold less, more preferably at least about 50-fold.

At high concentrations, some of the block copolymers utilized in the invention will form gels. These gels are viscous systems in which the translational and rotational freedom of the copolymer molecules is significantly constrained by a continuous network of interactions among copolymer molecules. In gels, microsegregation of the B block repeating units may or may not occur. To avoid the formation of gels, polymer concentrations (for both block copolymers and polyether/polycation polymers) will preferably be below about 15% (w/v), more preferably below about 10%, still more preferably below about 5%. In the first embodiment of the invention, it is more preferred that gels be avoided.

When the polynucleotide composition includes cationic components, the cations will associate with the phosphate groups of the polynucleotide, neutralizing the charge on the phosphate groups and rendering the polynucleotide component more hydrophobic. The neutralization is preferably supplied by cations on R-type polymeric segments or on polycationic polymers. However, the phosphate charge can also be neutralized by chemical modification or by association with a hydrophobic cations such as N-[1-(2,3-dioleyloxy)-propyl]-N,N,N,-trimethylammonium chloride]. In aqueous solution, the charge-neutralized polynucleotides are believed to participate in the formation of supramolecular, micelle-like particles, termed "polynucleotide complexes." The hydrophobic core or the complex comprises the charge-neutralized polynucleotides and the B-type copolymer blocks. The hydrophilic shell comprises the A-type copolymer blocks. The size of the complex will generally vary from about 10 nm to about 100 nm in diameter. In some contexts, it is practical to isolate the complex from unincorporated components. This can be done, for instance, by gel filtration chromatography.

The ratio of the components of the polynucleotide composition is an important factor in optimizing the effective transmembrane permeability of the polynucleotides in the composition. This ratio can be identified as ratio Ø, which is the ratio of positively charged groups to negatively charged groups in the composition at physiological pH. If Ø<1, the complex contains non-neutralized phosphate from the polynucleotide. The portions of the polynucleotides adjacent to the non-neutralized charges are believed to be a part of the shell of a polynucleotide complex. Correspondingly, if Ø>1, the polycationic polymer or R-type segment will have non-neutralized charges, and the un-neutralized portions will fold so that they form a part of the shell of the complex. Generally, Ø will vary from about 0 (where there are no cationic groups) to about 100, preferably Ø will range between about 0.01 and about 50, more preferably, between about 0.1 and about 20. Ø can be varied to increase the efficiency of transmembrane transport and, when the composition comprises polynucleotide complexes, to increase the stability of the complex. Variations in Ø can also affect the biodistribution of the complex after administration to an animal. The optimal Ø will depend on, among other things, (1) the context in which the polynucleotide composition is being used, (2) the specific polymers and oligonucleotides being used, (3) the cells or tissues targeted, and (4) the mode of administration.

Surfactant-Containing Polynucleotide Compositions. The invention also includes compositions of polynucleotides, cationic copolymer, and a suitable surfactant. The surfactant, should be (i) cationic (including those used in various transfection cocktails), (ii) nonionic (e.g., Pluronic or Tetronic), or (iii) zwitterionic (including betains and phospholipids). These surfactants increase solubility of the complex and increase biological activity of the compositions.

Suitable cationic surfactants include primary amines, secondary amines, tertiary amines (e.g., N,N',N'-polyoxyethylene(10)-N-tallow-1,3-diaminopropane), quaternary amine salts (e.g., dodecyltrimethylammonium bromide, hexadecyltrimethylammonium bromide, mixed alkyltrimethylammonium bromide, tetradecyltrimethylammonium bromide, benzalkonium chloride, benzethonium chloride, benzyldimethyldodecylammonium chloride, benzyldimethylhexa-decylammonium chloride, benzyltrimethylammonium methoxide, cetyldimethylethylammonium bromide, dimethyldioctadecyl ammonium bromide, methylbenzethonium chloride, decamethonium chloride, methyl mixed trialkyl ammonium chloride, methyl trioctylammonium chloride, N,N-dimethyl-N-[2-(2-methyl-4-(1,1,3,3-tetramethylbutyl)-phenoxyethoxy)ethyl] benzenemethanaminium chloride (DEBDA), dialkyldimetylammonium salts, N-[1-(2,3-dioleyloxy)-propyl]-N,N,N,-trimethylammonium chloride, 1,2-diacyl-3-(trimethyammonio)propane (acyl group=dimyristoyl, dipalmitoyl, distearoyl, dioleoyl), 1,2-diacyl-3-(dimethylammonio)propane (acyl group=dimyristoyl, dipalmitoyl, distearoyl, dioleoyl), 1,2-dioleoyl-3-(4'-trimethylammonio)

butanoyl-syn-glycerol, 1,2-dioleoyl-3-succinyl-syn-glycerol choline ester, cholesteryl (4'-trimethylammonio) butanoate), N-alkyl pyridinium salts (e.g. cetylpyridinium bromide and cetylpyridinium chloride), N-alkylpiperidinium salts, dicationic bolaform electrolytes ($C_{12}Me_6$; $C_{12}Bu_6$), dialkylglycerylphosphorylcholine, lysolecithin, L-α-dioleoyl phosphatidylethanolamine), cholesterol hemisuccinate choline ester, lipopolyamines (e.g., dioctadecylamidoglycylspermine (DOGS), dipalmitoyl phosphatidylethanolamidospermine (DPPES), lipopoly-L(or D)-lysine (LPLL, LPDL), poly(L (or D)-lysine conjugated to N-glutarylphosphatidylethanolamine, didodecyl glutamate ester with pendant amino group ($C_{12}GluPhC_nN^+$), ditetradecyl glutamate ester with pendant amino group ($C_{14}GluC_nN^+$), cationic derivatives of cholesterol (e.g., cholesteryl-3β-oxysuccinamidoethylenetrimethylammonium salt, cholesteryl-3β-oxysuccinamidoethylenedimethylamine, cholesteryl-3β-carboxyamidoethylenetrimethylammonium salt, cholesteryl-3β-carboxylamido-ethylenedimethylamine, 3β[N-(N',N'-dimethylaminoetane-carbamoyl] cholesterol).

Suitable non-ionic surfactants include n-Alkylphenyl polyoxyethylene ether, n-alkyl polyoxyethylene ethers (e.g., Tritons™), sorbitan esters (e.g., Spans™), polyglycol ether surfactants (Tergitol™), polyoxyethylenesorbitan (e.g., Tweens™), polysorbates, polyoxyethylated glycol monoethers (e.g., Brij™, polyoxylethylene 9 lauryl ether, polyoxylethylene 10 ether, polyoxylethylene 10 tridecyl ether), lubrol, copolymers of ethylene oxide and propylene oxide (e.g., Pluronic™, Pluronic R™, Teronic™, Pluradot™), alkyl aryl polyether alcohol (Tyloxapol™), perfluoroalkyl polyoxylated amides, N,N-bis[3-D-gluconamidopropyl] cholamide, decanoyl-N-methylglucamide, n-decyl α-D-glucopyranoside, n-decyl β-D-glucopyranozide, n-decyl β-D-maltopyranozide, n-dodecyl β-D-glucopyranozide, n-undecyl β-D-glucopyranozide, n-heptyl β-D-glucopyranozide, n-heptyl β-D-thioglucopyranozide, n-hexyl β-D-glucopyranozide, n-nonanoyl β-D-glucopyranozide 1-monooleyl-rac-glycerol, nonanoyl-N-methylglucamide, n-dodecyl α-D-maltoside, n-dodecyl β-D-maltoside, N,N-bis[3-gluconamidepropyl]deoxycholamide, diethylene glycol monopentyl ether, digitonin, heptanoyl-N-methylglucamide, heptanoyl-N-methyl-glucamide, octanoyl-N-methylglucamide, n-octyl β-D-glucopyranozide, n-octyl α-D-glucopyranoside, n-octyl β-D-thiogalactopyranozide, n-octyl β-D-thioglucopyranozide.

Suitable zwitterionic surfactants include betaine ($R_1R_2R_3N^+R'CO_2^-$, where $R_1R_2R_3R'$ are hydrocarbon chains and $R_1$ is the longest one), sulfobetaine ($R_1 R_2R_3N^+ R'SO_3^-$), phospholipids (e.g., dialkyl phosphatidylcholine), 3-[(3-cholamidopropyl)-dimethylammonio]-2-hydroxy-1-propanesulfonate, 3-[(3-chol-amidopropyl)-dimethylammonio]-1-propanesulfonate, N-decyl-N,N-dimethyl-3-ammonio-1-propanesulfonate, N-dodecyl-N, N-dimethyl-3-ammonio-1-propane-sulfonate, N-hexadecyl-N,N-dimethyl-3-ammonio-1-propanesulfonate, N-octadecyl-N,N-dimethyl-3-ammonio-1-propanesulfonate, N-octyl-N,N-dimethyl-3-ammonio-1-propanesulfonate, N-tetradecyl-N, N-dimethyl-3-ammonio-1-propanesulfonate, and dialkyl phosphatitidylethanolamine.

Polynucleotides/Nucleic acids. A wide variety of polynucleotides or nucleic acid molecules can be the polynucleotide component of the compositions. These include viruses, natural and synthetic DNA or RNA molecules, analogs thereof, and derivatives thereof, and nucleic acid molecules that have been covalently modified (to incorporate groups including lipophilic groups, photo-induced crosslinking groups, alkylating groups, organometallic groups, intercalating groups, lipophilic groups, biotin, fluorescent, and radioactive groups, and groups that modify the phosphate backbone). Such nucleic acid molecules are, but not_limited to, antisense nucleic acid molecules, viruses, viral vectors, gene-encoding DNA (usually including an appropriate promoter sequence), ribozymes, aptamers, anitgen nucleic acids, oligonucleotide α-anomers, ethylphosphotriester analogs, alkylphosphomates, phosphorothionate and phosphorodithionate oligonucleotides, and the like. Further, the polynucleotides can be nucleic acid molecules encoding a secreted or non-secreted protein or peptide, vaccines or antigens. In fact, the nucleic acid component can be any nucleic acid that can beneficially be transported into a cell with greater efficiency, or stabilized from degradative processes, or improved in its biodistribution after administration to an animal.

Targeting molecules. It will in some circumstances be desirable to incorporate, by noncovalent association, targeting molecules. See for example, Kabanov et al., *J. Controlled Release*, 22:141 (1992), the contents of which are hereby incorporated by reference. The targeting molecules that can be associated with the composition typically have a targeting group having affinity for a cellular site and a hydrophobic group. The targeting molecule will spontaneously associate with the polynucleotide complex and be "anchored" thereto through the hydrophobic group. These targeting adducts will typically comprise about 10% or less of the copolymers in a composition.

In the targeting molecule, the hydrophobic group can be, among other things, a lipid group such as a fatty acyl group. Alternately, it can be a block copolymer or another natural synthetic polymer. The targeting group of the targeting molecule will frequently comprise an antibody, typically with specificity for a certain cell surface antigen. It can also be, for instance, a hormone having a specific interaction with a cell surface receptor, or a drug having a cell surface receptor. For example, glycolipids could serve to target a polysaccharide receptor. It should be noted that the targeting molecule can be attached to any of the polymer blocks identified herein, including R-type polymeric blocks and to the polycationic polymers. For instance, the targeting molecule can be covalently attached to the free-terminal groups of the polyether segment of the block copolymer of the invention. Such targeting molecules can be covalently attached to the —OH end group of the polymers of the formulas XVIII, XIX, XX, and XXI, and the —NH$_2$ end group of the polymers of formulas XVIII (preferably the ε-amino group of the terminal lysyl residue), XX or XXIII, or the —COOH end group of the polymers of formulas XVIII and XIX. Targeting molecules can be used to facilitate intracellular transport of the polynucleotide composition, for instance transport to the nucleus, by using, for example, fusogenic peptides as targeting molecules described by Soukchareun et al., *Bioconjugate Chem.*, 6:43 (1995), or Arar et al., *Bioconjugate Chem.*, 6:43 (1995), caryotypic peptides, or other biospecific groups providing site-directed transport into a cell (in particular, exit from endosomic compartments into cytoplasm, or delivery to the nucleus).

The polynucleotide component of the compositions can be any polynucleotide, but are preferably a polynucleotide with at least about 3 bases, more preferably at least about 5 bases. Still more preferred are at least 10 bases. Included among the suitable polynucleotides are viral genomes and viruses (including the lipid or protein viral coat). This includes viral vectors including, but not limited to, retroviruses, adenoviruses, herpes-virus, or Pox-virus. Other suitable viral vectors for use with the present invention will be obvious to those skilled in the art. The terms "poly(nucleic acid)" and "polynucleotide" are used interchangeably herein. An oligonucleotide is a polynucleotide, as are DNA and RNA.

A polynucleotide derivative is a polynucleotide having one or more moieties (i) wherein the moieties are cleaved, inactivated or otherwise transformed so that the resulting material can function as a polynucleotide, or (ii) wherein the moiety does not prevent the derivative from functioning as a polynucleotide.

Therapeutic applications. The present compositions can be used in a variety of treatments. In a preferred embodiment, the compositions are used to induce activation or proliferation of dendritic cells and to increase the immune response in animals by administering the above described compositions. Preferably, the compositions for inducing activation of dendritic cells comprise a polynucleotide and at least one polyoxyethylene-polyoxypropylene block copolymer. More preferably, the block copolymers are PLURONIC F127 and L61. In an even more preferred embodiment, the block copolymers are a mixture of about 2% w/v F127 and 0.025% L61. In other specific embodiments, the block copolymers are a 10 fold dilution of PLURONIC F127/PLURONIC L61, and in another embodiment the block copolymers are a 100 fold dilution of PLURONIC F127/PLURONIC L61. In another specific embodiment, the block copolymers are a mixture of PLURONIC F127 and L61 in a ratio of 8:1.

For example, the compositions can be used in gene therapy including gene replacement or excision therapy, and gene addition therapy (B. Huber, Gene therapy for neoplastic diseases; B. E. Huber and J. S. Lazo Eds., The New York Academy of Sciences, N.Y., N.Y., 1994, pp. 6-11). Also, antisense therapy targets genes in the nucleus and/or cytoplasm of the cell, resulting in their inhibition (Stein and Cheng, Science 261:1004 (1993); De Mesmaeker et al., Acc. Chem. Res., 28:366 (1995)). Aptamer nucleic acid drugs target both intra-and extracellular proteins, peptides and small molecules. See Ellington and Szostak, Nature (London), 346:818 (1990). Antigen nucleic acid compounds can be used to target duplex DNA in the nucleus. See Helene and Tolume, Biochim, Biophys., Acta 1049:99 (1990). Catalytic polynucleotides target mRNA in the nucleus and/or cytoplasm. Cech, Curr. Opp. Struct. Biol., 2:605 (1992).

Examples of genes to be replaced, inhibited and/or added include genes encoding therapeutic secreted proteins, non-secreted proteins, vaccines and antigens, adenosine deaminase, tumor necrosis factor, cell growth factors, Factor IX, interferons (such as α-, β-, and γ-interferon), interleukins (such interleukin 2, 4, 6, and 12), HLA-B7, HSV-TK, CFTR, HIV-1, β-2, microglobulin, retroviral genes (such as gag, pot env, tax, and rex), cytomegalovirus, herpes viral genes (such as herpes simplex virus type I and II genes ICP27/UL54, ICP22/US1, ICP/IE175, protein kinase and exonuclease/UL13, protein kinase/US3, ribonuclease reductase ICP6/UL39, immediate early (IE) mRNA IE3/IE175/ICP4, 1E4/ICP22/US1, IE5/ICP47, IE110, DNA polymerase/UL30, UL13), human multidrug resistance genes (such as mdrl), oncogenes (such as H-c-ras, c-myb, c-myb, bcl-2, bcr/abl), tumor suppressor gene p53, human MHC genes (such as class 1 MHC), immunoglobulins (such as IgG, IgM, IgE, IgA), hemoglobin α- and β-chains, enzymes (such as carbonic anhydrase, triosephoshate isomerase, GTP-cyclhydrdolase I, phenylalanine hydrolase, sarcosine dehydrogenase, glucocerobrosidase, glucose-6-phosphste dehydrogenase), dysotrophin, fibronectin, apoliprotein E, cystic fibrosis transmembrane conductance protein, c-src protein, V(D)J recombination activating protein, immunogenes, peptide and protein antigens ("DNA vaccines") and the like.

More than one plasmid or gene can be expressed according to this invention. This can include at least one gene expressing an antigen and at least one gene expressing a molecule that can activate dendritic cells or other antigen presenting cells and thus serve as an adjuvant for enhanced antigen presentation and induced immune response; e.g. a cytokine. Examples of such adjuvants include but are not limited to interleukins, such as interleukin-12, FIt3 ligand, GM-CSF, CD40 ligand. The antigen can be any product for which an immune response is produced. In addition, either antigen or adjuvant protein can be added in combination with the gene therapy. For example, FLT-3 ligand can be injected in the body with the plasmid or retrovirus encoding the antigen.

A MIXTURE OF PLURONIC F127/PLURONIC L61 has the capability to induce NF-κB-driven genes known like cytokines and chemokines that are to provoke infiltration of dendritic cells. As shown below, SP1O17 has a promoter dependence and seems to favor activation of the transcription factor NF-κB. Studies have demonstrated that DNA constructs driven by CMV promoter or NF-κB-sensitive element cassette are considerably more responsive to the PLURONIC F127/PLURONIC L61 carrier effect compared to the constructs under SV-40 promoter or AP-1-sensitive cassette, suggesting that in addition to the delivery effect, PLURONIC F127/PLURONIC L61 acts as a biological response modifier by interfering with transcriptional control of the transgene expression.

The p65 subunit of NF-κB (also known as ReIA, NFκB3 and NF-κB p65 subunit) is a member of the Rel/NF-κB family of transcription factors which includes p50, cRel, p52 and RelB. NF-κB p65 subunit was first isolated from Jurkat T cells using a probe that spanned a conserved domain to the proto-oncogene cRel (Ruben et al., Science, 1991, 251, 1490-1493) and since that time, a naturally occurring transforming variant of the protein has been shown to exist (Narayanan et al., Science, 1992, 256, 367-370). In addition, the NF-κB binding DNA sequence has been found in various genes and it has been shown that it is actually important for the expression of the function of genes. The binding sequence of NE-κB (κB motifs) is composed of about 10 bases having a common sequence which starts with a cluster of G (guanine) and ends with a cluster of C (cytosine) (consensus sequence 5'-GGGRNNYCCC-3'). (SEQ ID NO 1) However, a number of sequences to which DNA binding proteins can be bonded are present on the genes of interleukin-1 (to be referred to as IL-1 hereinafter in some cases) and tumor necrosis factor (to be referred to as TNF hereinafter in some cases) which are known as inflammatory proteins, and it is known that the NF-κB binding sequence is also present therein (Clark, B. D. et al., Nuci. Acids Res., 14, 7898, 1984; Nedospasov, S. A. et al., Cold Spring Harb. Symp. Quant. Bid., 51, 611, 1986). It has been reported that the binding of NF-κB inhibits transcription to mRNA (Hiscott, J. et al., Mol. Cell. Biol., 13, 6231, 1993; Collart, M. A. et al., Mol. Cell. Biol., 10, 1498, 1990).

Genetic diseases can also be treated by the instant compositions. Such diseases include, rheumatoid arthritis, psoriasis, Crohn's disease, ulcerative colitis, α-thalassemia, β-thalassemia, carbonic anhydrase II deficiency syndrome, triosephosphate isomerase deficiency syndrome, tetrahydrobiopterindeficient hyperphenylalaniemia, classical phenylketonuria, muscular dystrophy such as Duchenne Muscular Dystrophy, hypersarkosinemia, adenomatous intestinal polyposis, adenosine deaminase deficiency, malignant melanoma, glucose-6-phosphste dehydrogenase deficiency syndrome, arteriosclerosis and hypercholesterolemia, Gaucher's disease, cystic fibrosis, osteopetrosis, increased spontaneous tumors, T and B cell immunodeficiency, high cholesterol, arthritis including chronic rheumatoid arthritis, glaucoma, alcoholism and the like.

The compositions can also be used to treat neoplastic diseases including, but not limited to, breast cancer (e.g., breast, pancreatic, gastric, prostate, colorectal, lung, ovarian), lymphomas (such as Hodgkin and non-Hodgkin lymphoma), melanoma and malignant melanoma, advanced cancer hemophilia B, renal cell carcinoma, gliblastoma, astrocytoma, gliomas, AML and CML and the like.

Additionally, the compositions can be used to treat (i) cardiovascular diseases including but not limited to stroke, cardiomyopathy associated with Duchenne Muscular Dystrophy, myocardial ischemia, restenosis and the like, (ii) infectious diseases such as Hepatitis, HIV infections and AIDS, Herpes, CMV and associated diseases such as CMV renitis, (iii) transplantation related disorders such as renal transplant rejection and the like, and (iv) are useful in vaccine therapies and immunization, including but not limited to melanoma vaccines, HIV vaccines, malaria, tuberculosis, and the like. The compositions are useful in all applications where polynucleotides and viruses are used for vaccination and immunization.

Target Cells. The present invention is also directed to a method of delivering a polynucleotide to a cell comprising administering a composition of the present invention. In one embodiment, the method of delivering a polynucleotide to a cell comprises administering a composition comprising a polynucleotide or derivative thereof and at least one polyethylene-polypropylene block copolymer, wherein the block copolymer is present in amounts insufficient for gel formation. In another embodiment, the block copolymer is present at a concentration below about 15% wt/vol, more preferably at a concentration below about 10% wt/vol, and most preferably, in concentrations below about 5%. A further embodiment, the composition forms a molecular solution or colloidal dispersion, more particularly, the colloidal dispersion is a suspension, emulsion, microemulsion, micelle, polymer complex or other types of molecular aggregates.

Target cells for the delivery of a polynucletide composition are, but not limited to, dendritic cells procaryotic or eucaryotic cells, preferably animal cells, more preferably mammalian cells, and most preferably human cells. Cell targets can be ex vivo and/or in vivo, and include T and B lymphocytes, primary CML, tumor infiltrating lymphocytes, tumor cells, leukemic cells (such as HL-60, ML-3, KG-1 and the like), skin fibroblasts, myoblasts, cells of central nervous system including primary neurons, liver cells, carcinoma (such as Bladder carcinoma T24, human colorectal carcinoma Caco-2), melanoma, CD34+ lymphocytes, NK cells, macrophages, hemotopoetic cells, neuroblastona (such as LAN-5 and the like), gliomas, lymphomas (such as Burkitt lymphomas ST486), JD38), T-cell hybridomas, muscle cells such as primary smooth muscle, and the like.

Methods of use. The polynucleotide compositions of the present invention can be used for treatment of animals, including, but not limited to animals such as chickens, pigs, cows, cats, dogs, horses, fish, shrimp, and preferably to mammals, and most preferably humans. The polynucleotide compositions of the invention can be administered orally, topically, rectally, vaginally, by pulmonary route by use of an aerosol, or parenterally, i.e. intramuscularly, intradermally, subcutaneously, intraperitoneally or intravenously.

For inducing activation of dendritic cells and for increasing the immune response in an animal, the preferred routes of administration include, but are not limited to intravenous, oral, intradermal, intramuscularly, subcutaneously ot intraperitonenely. Preferably, the route of administration is direct injection into the tumor. The polynucleotide compositions can be administered alone, or it can be combined with a pharmaceutically-acceptable carrier or excipient according to standard pharmaceutical practice. For oral administration, the polynucleotide compositions can be used in the form of tablets, capsules, lozenges, troches, powders, syrups, elixirs, aqueous solutions and suspensions, and the like. In the case of tablets, carriers that can be used include lactose, sodium citrate and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, the polynucleotide compositions can be combined with emulsifying and suspending agents. If desired, sweetening and/or flavoring agents can be added. For parenteral administration, sterile solutions of the conjugate are usually prepared, and the pH of the solutions are suitably adjusted and buffered. For intravenous use, the total concentration of solutes should be controlled to render the preparation isotonic. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or poly (vinyl alcohol), preservatives such as sorbic acid, EDTA or benzylchronium chloride, and the usual quantities of diluents and/or carriers. For pulmonary administration, diluents and/or carriers will be selected to be appropriate to allow the formation of an aerosol.

For intramuscular administration, the formulation of the polynucleotides will be without any polycationic moiety since naked polynucleotides itself can be transferred and expressed in muscle without any polycation-containing delivery systems. The muscle has the following features: unique cytoarchitecture, multiple nuclei per myotubes, specific-polynucleotides binding proteins (triadin), and unique nucleocytoplasmic transport. At present, it is still unclear as to which features listed above may be responsible for the uptake and expression of naked polynucleotides in muscle. Cationic complexes of polynucleotides have been shown to enhance uptake and gene expression in virtually all tissue types but surprisingly the same complexes do not contribute to a better uptake and gene expression in muscle. In fact, cationic complexation of polynucleotides inhibit uptake and gene expression in muscle and reported by several laboratories. Thus, for intramuscular injection of polynucleotides, complexation of polynucleotides should be avoided. This invention uses nonionic block copolymers for intramuscular delivery of polynucleotides. Block copolymers alone are totally inefficient at transferring genetic material in cells in vitro and in vivo (see example 42). Moreover, unlike polycation-containing block copolymers, the above nonionic block copolymers do not increase gene expression in the peripheral organs such as lungs, liver, kidneys.

The following examples will serve to further typify the nature of the invention but should not be construed as a limitation on the scope thereof.

EXAMPLE 1

Transfection Efficiencies

This experiment introduced plasmid pβ-Gal into NIH 3T3 cells, a mouse mammary tumor cell line. Plasmid pβ-Gal comprises plasmid pUC19 (available from the Institute of Gene Biology, Russian Academy of Sciences) into which a hybrid of a eukaryotic transcription unit and a *E. coli* β-galactosidase has been incorporated. With this plasmid, the efficiency of cell uptake can be measured by measuring β-galactosidase activity extractable from the treated cells. The copolymer utilized was a triblock copolymer of formula (XIV) wherein x plus z was 51 and y was 39 (hereinafter "Pluronic A"). The polycation used was poly(N-ethyl-4-vinylpyridinium bromide) ("pEVP-Br"). A 10 µg/ml solution of pβ-Gal (predominantly supercoiled) was prepared in a solution of PBS containing 10 mg/ml of Pluronic A and 45 µg/ml of pEVP-Br. These amounts were calculated to provide a ratio of polycation basic groups to plasmid phosphate groups of about 10. The ratio of Pluronic A to DNA was about $10^4$. This stock preparation was filter sterilized and a portion was diluted ten fold with serum-free Dulbecco's Modified Eagle's Medium ("DMEM"), so that the concentration of pβ-Gal was 1 µg/ml. This solution was the "Pluronic A transfecting medium."

The NIH 3T3 cells were grown in monolayer culture at 37° C. under 5% $CO_2$, using a DMEM medium containing 2 mM glutamine and 10% fetal calf serum ("FCS"). Cells were grown in monolayer culture were scraped and prepared for the transaction process by washing three times with fresh medium.

Aliquots of washed cells that were to be transformed by the method of the invention were suspended at a concentration of $10^6$ cells/ml in Pluronic A transfecting medium. The suspended cells were incubated for 2 hours at 37° C. and under 5% $CO_2$. The cells were then washed with fresh medium and re-plated.

Aliquots of cells that were to be transfected by calcium phosphate precipitation were transfected as recommended by Promega of Madison, Wis., in their manuscript *Profection Mammalian Transfection Systems*, Technical Manual, 1990. Specifically, pβ-Gal was mixed with 0.25M $CaCl_2$. The mixture was mixed with an equal volume of 2×HBS (Hanks Buffer Salt, available from GIBCO, Grand Island, N.Y.) to create a mixture containing 1 µg/mL pβ-Gal. The opaque mixture was incubated at room temperature for 10 minutes and then applied to the cells. The suspended cells were incubated for 2 hours at 37° C. and under 5% $CO_2$. The cells were then washed with fresh medium and re-plated.

The repeated cells were incubated for 48 hours in DMEM medium containing 10% FCS. During the incubation, the medium was replaced with fresh medium at 16 hours. After the 48 hour incubation, the cells for each incubation were collected by scrapping, washed with PBS, and resuspended in 100 µl of 0.2 M Tris-HCL (pH 7.4). The cells were lysed with several freeze/thaw cycles, and centrifuged at an excess of 6,000×/g. 50 µl of supernatant was removed from each lysate tube and mixed with 50 µl of a solution of 0.1 mM 4-methyl-umbelliferril-β-D-galactopiraniside (the substrate), 0.1 M sodium phosphate (pH 7.4). Each mixture was incubated for 20 min. at 37° C. to allow any β-galactosidase present to act on the substrate. 50 µl of 0.4 M glycine, pH 10.5, was added to terminate the β-galactosidase reaction. β-galactosidase activity was indicated by the presence of methylbelliferon, which can be measured by fluorescence spectroscopy ($\lambda_{ex}$=365 nm, λ=450 nm). The results were as follows:

| Treatment | Relative Enzyme Activity ± SEM (n = 4) |
|---|---|
| Pluronic A | 320 ± 42 |
| Calcium Phosphate Precipitation | 17 ± 5 |

EXAMPLE 2

Transfection Efficiencies

In these experiments, transfection efficiencies with MDCK cells (derived from canine kidney) were examined. As above, pβ-Gal was the indicator polynucleotide. The polycation component of the polynucleotide comprised a copolymer of N-ethyl-4-vinylpyridinium bromide and N-cetyl-4-vinylpyridinium bromide, the monomers incorporated in a molar ratio of 97:3, respectively (hereinafter "pEVP-co-pCVP-Br"). The block copolymer comprised a triblock copolymer of formula (XIV) wherein x+z was 18, and y was 23 (hereinafter "Pluronic B"). A Pluronic B transfecting solution of 1 µg/ml pβ-Gal, 3 µg/ml PEVP-co-pCVP-Br, and 1% (w/v) Pluronic B was prepared in Example 1. The ratio of polycation basic groups to nucleotide Phosphates was about 7. The weight ratio of Pluronic B to pβ-Gal was about $5\times10^3$.

MDCK cells were plated at 8-$10^5$ cells per plate onto 90 mm plates and incubated overnight under serum-containing growth medium. The serum containing medium was then replaced with serum-free medium, and the cells were incubated at 37° C., under 5% $CO_2$ for 24 hours. For the cells to be treated with polynucleotide complex, the medium was then replaced with 5 ml Pluronic B transfecting solution. The cells were incubated, with gentle rocking, at 37° C., under 5% $CO_2$ In control experiments, cells were transfected with polynucleotide complex, the medium was then replaced with 5 ml Pluronic B transfecting solution. The cells were incubated, with gentle rocking, at 37° C., under 5% $CO_2$, for 2 hours. In control experiments, cells were transfected using the calcium phosphate procedure as described above (except that plated cells, not suspended cells, were transfected).

After treatment with Pluronic B transfecting solution or calcium phosphate, the cells were washed 5-6 times with fresh medium. They were then incubated in DMEM containing 10% FCS for 48 hours at 37° C., under 5% $CO_2$. After the first 16 hours of this incubation, the medium was replaced. After the incubation, the cells were washed with PBS, released from their plates by trypsinization, and again washed with PBS. β-Galactosidase was measured as described for Example 1. The results were as follows:

| Treatment | Relative β-galactosidase activity ± SEM (n = 4) |
|---|---|
| Pluronic B | 910 ± 45 |
| Calcium Phosphate Precipitation | 81 ± 17 |

EXAMPLE 3

Transfection Experiments

In these experiments, transfection efficiencies with Chinese hamster ovary (CHO) cells were examined. The polynucleotic component of the polynucleotic complex was pβ-Gal. The polycation component comprised pEVPBr. The block copolymer comprised an octablock copolymer formula (XVII), wherein i was equal to 10 and j was equal to 12 (hereinafter "Pluronic C" available from BASF). A Pluronic C transfecting solution of 1 μg/ml pβ-Gal, 4 μg/ml pEVP-Br, and 1% (w/v) Pluronic C was prepared as in Example 1. The ratio of basic groups to nucleotide phosphates was 10. The weight ratio of Pluronic C to pβ-Gal was $10^3$. The transfection protocol was the same as that used in Example 2. The results were as follows:

| Treatment | Relative β-galactosidase activity ± SEM (n = 4) |
|---|---|
| Pluronic B | 910 ± 45 |
| Calcium Phosphate Precipitation | 81 ± 17 |

EXAMPLE 4

Bacterial Transformation

In these experiments, transformation efficiencies using the MC5 strain of *Bacillus subtilis* were examined. The polynucleotide component of the polynucleotide complex was plasmid pBC16, a plasmid encoding tetracycline resistance. A block copolymer according to formula (VI) was used. In particular, the block copolymer was a poly(oxyethylene)-poly((N-ethyl-4-vinylpyridinium bromide) of formula (XXI), wherein i was 44, and j was 20. A stock solution of second embodiment polynucleotide complex was prepared consistent with the transfection solutions described above. The ratio of copolymer basic groups to DNA phosphates in the solution was 0.2. Bacteria were suspended in Spizizen 11, a transformation media (see, Spizizen, *F.N.A.S., U.S.A.* 44:1072 (1958)), and aliquots of cells were incubated in varying concentrations of either polynucleotide complex or free pBC16. The cells were incubated with complex or free DNA for one hour at 37° C. Following the incubation, the cells were plated onto agar media containing 10 mg/ml tetracycline. The results, measured by the number of tetracycline-resistant colonies produced under each of the experimental conditions, were as follows:

| | Transformation ($10^6$ clones/ng DNA) | |
|---|---|---|
| DNA concentration (ng/ml) | Polynucleotide Complex | Free Polynucleotide |
| 5 | 300 (±15) | 0 |
| 10 | 450 (±22) | 3 (±1) |
| 20 | 400 (±26) | 3 (±4) |
| 50 | 220 (±17) | 20 (±5) |

EXAMPLE 5

Protection from Nuclease

For this example, a complex of plasmid pTZ19 and a diblock copolymer of formula (XXI) (poly(oxyethylene)-poly((N-ethyl-4vinylpyridinium bromide), wherein i was 44 and j was 20) was formed. The solution of polynucleotide complex dissolved in PBS contained about 4 μg/ml of plasmid and 20 μg/ml of diblock copolymer. These amounts resulted in a ratio of base groups in the polycation block to DNA phosphate groups of 5. For control incubations, an equivalent amount of free plasmid was dissolved in buffer. PVUII nuclease was added to solution samples containing free DNA or polynucleotide complex, and the amount of undigested, circular plasmid DNA, after various digestion times, was determined by electrophoresis in a polyacrylamide gel. See Kabanov et al. *Biopolymers*, 31:1437-1443 (1991). The results were as follows:

| | Circular DNA (% of initial) | |
|---|---|---|
| Time of Incubation | Complex | Free DNA |
| 0 | 100 | 100 |
| 5 | 100 | 20. |
| 10 | 100 | 8 |
| 30 | 100 | 4 |
| 60 | 100 | 1 |
| 180 | 100 | 0 |
| 600 | 100 | 0 |

EXAMPLE 6

Oligonucleotide Stabilization

For this example, a complex containing an oligonucleotide complementary to the transcription initiation site of the HIV-1 tat gene ("anti-tat", comprising GGCTCCATTTCT-TGCTC) (SEQ ID NO 2) was prepared using the diblock copolymer of formula (XIX) (polyoxyethylene-poly(L-alanine-L-lysine), wherein i is 44 and j is 8). The oligonucleotide complex was prepared in PBS Buffer (pH 7.0) at a concentration of 0.75 $OD_{260}$/μl oligonucleotide. The ratio of polycation imino and amino groups to polynucleotide phosphate groups was about 50. The mixture was incubated for one hour at room temperature to allow for the formation of the complex. Then, the complex was purified by gel filtration chromatography on Sephadex G-25 using 0.05 M NaCl as the eluent. The resulting solution of complex exhibited a concentration of 0.11 $OD_{260}$/μl of oligonucleotide. A comparable solution of uncomplex oligonucleotide was prepared. An aliquot of murine blood plasma (10 μl) was mixed with an equal volume of oligonucleotide complex solution or a solution of free oligonucleotide. Samples were incubated at 370° C. for various time periods. To stop the reaction of the oligonucleotides with enzymes in the plasma, the samples were diluted with water and extracted with a water-saturated mixture of phenol:chloroform (1:1). The aqueous phase of the extraction was isolated, and the oligonucleotide therein was precipitated with 3% lithium Perchiorate. The precipitate was washed with acetone, and then dissolved in 100 μl of water. The presence of undergraded oligonucleotide was determined by high performance liquid chromatography using a $C_{18}$-Silasorb column (4×90 mm, Gilson, France) and a gradient of acetonitrile in 0.05 M triethyl-ammoniumacetate (pH 7.0) as the eluent. The results were as follows:

| Time of | Undergraded oligonucleotide (%) | |
|---|---|---|
| Incubation | Complex | Free Oligo |
| 0 | 100 | 100 |
| 3 hours | 88 | 28 |
| 6 hours | 70 | 17 |
| 24 hours | 36 | 0 |

EXAMPLE 7

Oligonucleotide Stabilization

This example examined the stability of the oligonucleotide described in Example 6, when complexed with a diblock copolymer of formula (XX) (polyoxyethylene-polypropyleneimine/butyleneimine, wherein i is 44 and j is 4-8) was examined. The same methodologies that were applied in Example 6 were applied for this example, except that the oligonucleotide concentration was about 0.13 $OD_{260}/\mu l$. The results were as follows:

| Time of | Undergraded oligonucleotide (%) | |
|---|---|---|
| Incubation | Complex | Free Oligo |
| 0 | 100 | 100 |
| 3 hours | 70 | 28 |
| 6 hours | 57 | 17 |
| 24 hours | 28 | 0 |

EXAMPLE 8

Antisense Cell Incorporation Efficiencies

This experiment examined the effectiveness of "anti-MDR", an antisense molecule comprising a 17-chain oligonucleotide of sequence CCTTCAAGATCCATCCC (SEQ ID NO 3) complementary to positions 422-438 of the mRNA encoding the MDR1 gene product, in reversing multi-drug resistance in SKVLB cells. SKVLB cells are multi-drug resistant cells derived from a ovarian cancer cell line. The MDR1 gene has been identified as responsible for the multi-drug resistance in SKVLB cells. Endicott and Ling, *Ann. Rev. Biochem.*, 58:137 (1989). In particular, the efficiency of the anti-MDR oligonucleotide in the polynucleotide complex of the invention and when in the free state was compared. As controls, the free and completed form of the anti-tat oligonucleotide described above were also used. The polynucleotide complexes were formed with the diblock copolymer of formula (XX) (polyoxyethylenepolypropyleneimine/butyleneimine, where i was 44 and j was 9-10). The complexes were prepared by the procedures described in Example 6. The oligonucleotide concentration in the complex or in the free state was 0.17 $OD_{260}/\mu l$. The copolymer was present in the concentration sufficient to define a ratio of polycation block imino and amino groups to oligonucleotide phosphate groups of 10.

The SKVLB cells were incubated for 3 days at 37° C. under 5% $CO_2$ in the presence of free or completed oligonucleotide (at a concentration of 20 µM based on oligonucleotide content). Fresh media including free or completed oligonucleotide was added every 12 hours.

The daunomycin cytotoxicity ($IC_{50}$) with respect to the cells treated as described above was measured using the method of Alley et. al., *Cancer Res.*, 48:589-601. The results were as follows:

| Treatment of Cells | Daunomycin $IC_{50}$ (ng/ml) (n = 4) |
|---|---|
| Control (untreated cells) | 8.0 |
| Anti-MDR Complex | 0.3 |
| Anti-tat Complex | 8.2 |
| Free Anti-MDR | 2.1 |
| Free Anti-tat | 7.9 |

EXAMPLE 9

Antisense Oligonucleotide Designed to Inhibit Herpes Virus

This experiment used a 12-chain oligonucleotide, which had been covalently modified at its 5' end with undecylphosphate substituent and at is 3' end with a acridine group, was used. This oligonucleotide modification has been described by Cho-Chung et. al., *Biochemistry Int.*, 25:767-773 (1991). The oligonucleotide sequence utilized, CGTTCCTCCTGU, (SEQ ID NO 4) was complementary to the splicing site at 983-994 of the Herpes Simplex Virus 1 ("HSV-1"). As a control, an equivalently modified sequence (AGCAAAAG-CAGG) (SEQ ID NO 5) complementary to the RNA produced by influenza virus was utilized. The oligonucleotides were applied to HSV-1 infected cells in either the complexed or the free state. When a complex was utilized, the complex was formed with the diblock copolymer of formula (XIX) (polyoxyethylene-poly(L-alanine-L-lysine), wherein i was equal to 44 and j was equal to 8). Oligonucleotide complexes were formed as described in Example 6.

African marmoset kidney cells ("Vero" cells) were infected with HSV-1 virus (strain L2, obtained from the Museum of Virus Strains, D. I. Ivanovskii, *Inst. of Virol.*, Russian Federation), as described by Vinogradov et al. *BBRC*, 203:959 (1994). The infected cells were washed with PBS. After washing, fresh RPMI-L 640 media containing 10% of fetal calf serum and free or complex oligonucleotide was added to the cell. The cells were then incubated at 37° C. under 5% $CO_2$ for 24 hours. The HSV-1 infectivity of the of the cell media was then determined using the patch production method described by *Virology, A Practical Approach*, Mahy, Ed., IRL Press, Washington, D.C., 1985. The results, utilizing varying concentrations of oligonucleotide, were as follows:

| Oligo Conc. | HSV-1 Infectious Titre ($CPE_{50}/ml$) (n = 7) | | |
|---|---|---|---|
| Treatment | 0.2 µM | 1.0 µM | 5.0 µM |
| Control (untreated infected cells) | 1.0 (±0.5) × $10^6$ | 1.0 (±0.5) × $10^6$ | 1.0 (±0.5) × $10^6$ |
| Anti-HSV complex | 1.4 (±0.2) × $10^2$ | 0.5 (±0.3) × $10^2$ | 0 |
| Anti-influenza complex | 1.0 (±0.6) × $10^6$ | 0.7 (±0.1) × $10^6$ | 0.8 (±0.2) × $10^6$ |
| Free Anti-HSV | 0.9 (±0.4) × $10^5$ | 2.3 (±0.7) × $10^3$ | 1.6 (±0.4) × $10^2$ |
| Free Anti-Influenza | 1.1 (±0.4) × $10^6$ | 0.9 (±0.2) × $10^6$ | 0.6 (±0.3) × $10^6$ |

EXAMPLE 10

Antisense Oligonucleotide Designed to Inhibit Herpes Virus

Unless otherwise noted, this example utilized the same procedures as were utilized in Example 9. The cells utilized were BHK cells, a Chinese hamster kidney cell line. When the complexed form of the oligonucleotides was used, the complex was formed with the diblock copolymer of formula (XVII) (polyoxyethylene-poly-L-lysine, wherein i was 44 and j was 30), using the procedure described in Example 6. The concentration of the stock solution of complex was 0.09 $OD_{260}/\mu l$. The ratio of polycation block imino and amino groups to oligonucleotide phosphates was 10. The oligonucleotides, in complexed or free form, were applied to the cells at a concentration of 3.0 $\mu M$. The results were as follows:

| Treatment of cells | HSV-1 infectious titre ($CPE_{50}$/ml) n = 7 |
|---|---|
| Control (untreated infected cells) | 10 (±3) × $10^3$ |
| Anti-HSV complex | 8 (±6) |
| Anti-influenza complex | 13 (±4) × $10^3$ |
| Free Anti-HSV | 50 (±14) × $10^2$ |
| Free Anti-influenza | 9 (±2) × $10^3$ |

EXAMPLE 11

In Vivo Inhibition of HSV

Polynucleotide complexes between the block copolymer of formula (XVII) (polyoxyethylene-poly-L-lysine, wherein i was 44 and j was 30) and the Anti-HSV and Anti-influenza oligonucleotides were formed using the methods outlined in Example 9. The concentration of the stock solutions of complexes was 0.9 $OD_{260}/\mu l$. The ratio of polycation block imino and amino groups to oligonucleotide phosphates was 10.

Inbred white mice (body weight 6-7 g) were infected with HSV-1 (strain CI from *Belorussian Res. Inst. of Epidemiol. & Microbiol., Minsk*) by intraperitoneal injection of 30 µl of a virus suspension (titre: $10^{-7}$ $LD_{50}$/ml).

Either Anti-HSV complex, Anti-influenza complex, free Anti-HSV or free Anti-Influenza were injected (10 µl) into the tail vein of a given mouse at each of 2, 12, 24, 48, or 72 hours post-infection. The results were as follows:

| Treatmen | Animals Survived/No. of Animals in group | | | % Survival |
|---|---|---|---|---|
| | Exp. 1 | Exp. 2 | Exp. 3 | |
| Control (infected mice) | 1/9 | 1/10 | 2/10 | 13.7 |
| Anti-HSV complex | 8/9 | 6/10 | 7/10 | 73.0 |
| Anti-influenza complex | 2/10 | 0/10 | 1/10 | 10.0 |
| Free Anti-HSV | 1/10 | 1/10 | 0/10 | 7.0 |
| Free Anti-influenza | 0/9 | 1/10 | 0/10 | 7.0 |

EXAMPLE 12

Plasma Life of Polynucleotide Complex

A$^{32}$P-labelled 17-mer (GGCTCCATTTCTTGCTC) (SEQ ID NO 6) complementary to the transcription initiation site of the HIV-1 tat gene was utilized in this example. The oligonucleotide was modified at its 5'-end with cholesterol as described by Boutorin et al., *Bioconjugate Chemistry*, 2: 350-356 (1990). A polynucleotide conjugate of the oligonucleotide was formed with the block copolymer of formula (XX) polyoxyethylene-poly (propyleneimine/butyleneimine), wherein i was 44 and j was 9 to 10). The concentration of the stock solution (dissolved in PBS) of complex was 0.18 $OD_{260}/\mu l$. The ratio of polycation block imino and amino groups to oligonucleotide phosphates was 50.

Male C57/BI/6 mice (weight: 20-24 g; obtained from the Russian Research Center of Molecular Diagnostics and Therapy, Moscow) received 50 µl intravenous injections of Anti-HIV conjugate or free Anti-HIV, at 0.18 $OD_{260}/\mu l$ dissolved in PBS. At defined times after the injections, blood sample were taken from the tail vein and the animals were sacrificed. The amount of radioactive material in blood or tissue sample was determined by liquid scintillation counting (after appropriate solubilizations). The results were as follows:

| Time after injection (min) | Plasma levels (% of injected dose) | | Liver levels (% of injected dose) Prep. A | Liver levels (% of injected dose) Prep. B |
|---|---|---|---|---|
| | Anti-HIV Conjugate | Free Anti-HIV | | |
| 0 | 100 | 100 | 0 | 0 |
| 5 | 95 | 58 | 3 | 7 |
| 10 | 91 | 40 | 5 | 19 |
| 15 | 84 | 33 | 7 | 26 |
| 20 | 79 | 27 | 9 | 30 |
| 30 | 75 | 20 | 10 | 35 |

EXAMPLE 13

Cationic Block Copolymer Synthesis 1,4-dibromobutane (5.4 g, 25 mmoles, from Aldrich Co., Milwaukee, Wis.) was added to a solution of N-(3-aminopropyl)-1,3-propanediamine (6.55 g, 50 mmoles, from Aldrich Co.) dissolved in 100 ml of 1,4-dioxane. This reaction mixture was stirred at 20° C. for 16 h. The product of this reaction spontaneously precipitates from solution as the hydrobromide salt. This precipitated first intermediate was collected and twice dried by rota-evaporation from a solution of 10% triethylamine in methanol. This evaporation procedure was effective to remove substantial amounts of the bromide salt. The first intermediate was dissolved in 50 ml of 1,4-dioxane and reacted with 2.7 g (12.5 mmoles) of 1,4-dibromobutane. Again, the reaction proceeded for 16 h at 20° C., and the resulting second intermediate was recovered and dried as above.

The second intermediate was neutralized with acetic acid to a pH of 7-8 and purified by gel filtration on Sephadex G-25, using an aqueous eluent. Three major polymine fractions were obtained, having apparent molecular weights of 1060, 700 and 500, respectively.

Poly(oxyethyleneglycol) (1.5 g, M.W. 1500, from Fluka) was dissolved in 8 ml of 1,4-dioxane and reacted with 0.17 g (1 mmole) of N,N'-carbonylimidazole (Aldrich Co.) at 20° C. for 3 h. The reaction mixture was divided into two parts. Each part was mixed with 4 ml of a 10% (w/v) solution of either the 1060 or 700 MW polyimine fraction, which solution further contained 0.01 N NaOH. The mixture was stirred for 16 h at 20° C. From this mixture, block copolymers of formula (XX) and various MW ranges were isolated by gel filtration.

EXAMPLE 14

Cationic Block Copolymer Synthesis 0.5 g of a succinimidyl carbonate of methoxy-PEG (MW 5000, Shearwater Polymers, Inc., USA) was dissolved in 1,4-dioxane. This dioxane solution was added to an aqueous solution containing 0.2 g of the 1060 MW polyimine polymer described above, which aqueous solution further included 0.01 N NaOH. This reaction mixture was stirred at 20° C. for 16 h. A polymer of formula (XXII) was isolated from the reaction by gel filtration.

EXAMPLE 15

Cationic Block Copolymer Synthesis 1.5 g of poly(oxyethyleneglylol) (MW 8000, Fluka) were dissolved in 8 ml of 1,4-dioxane. 0.34 g (2 mmole) of N,N'-carbonylimidazole (Aldrich Co.) were added to the solution and reacted for 3 h at 20° C. 8 ml of an aqueous solution containing 0.01 N NaOH and 15% (w/v) of the 500 MW polyimine polymer described above in Example 13 was then added to the first reaction mixture. The resulting mixture was reacted for 16 h at 20° C. with stirring. A polymer of formula (XXIII) was isolated from the second reaction mixture by gel filtration.

EXAMPLE 16

Conjugate Synthesis with Oligonucleotide

A 12-mer oligonucleotide, 5'-CGTTCCTCCTGU ("Oligo A") (SEQ ID NO 4) complimentary to the splicing site (positions 983-994 on the viral genome) of the early mRNA of type 1 Herpes Simplex Virus ("HSV-1"), was synthesized using a 380B-02 DNA-synthesizer (Applied Biosystems, CA). The synthesizer used phosporamidite chemistry and an 8 mm. synthesis cycle. Cycle conditions and preparation of the crude product were done as recommended by Applied Biosystems. The crude Oligo A obtained from the synthesis was precipitated from a 1 M LiCl solution (0.5 ml) with acetone (2 ml). The precipitate was dissolved in triethylammonium acetate buffer and purified by reverse-phase high performance liquid chromatography on a Silasorb C18 column (9×250 mm, Gilson, France) developed with an acetonitrile gradient in a 20 mM TEAA buffer (pH 8.5).

The 3'-terminal of the purified Oligo A was oxidized with periodate to create an aldehyde and conjugated by reductive alkylation with a hexamethylene-diamine linker, creating an amine derivative. See Che-Chung et al. *Biochem. Internat.*, 25:767 (1991); Vinogradov et al., *BBRC,* 203:959 (1994). "Pluronic A", a block copolymer of formula (XIV)(x=25, y=38, z=25) was similarly oxidized to create terminal aldehydes. The amine derivative (1 mg) was dissolved in 100 μl of 0.1 M borate buffer (pH 9.0) and mixed with 2 mg of the Pluronic A derivative. 1.5 mg of sodium cyanoborohydride was added to the mixture to reduce the Schiff's bases formed between the amine and aldehyde groups. This reaction was allowed to proceed for 12 hours at 4° C. The polymeric product of this reaction was isolated by gel filtration chromatography on Sephadex LH-20, utilizing 90% aqueous isopropanol as the eluent. The conjugate so obtained is referred to hereinafter as "Oligo A Conjugate."

EXAMPLE 17

The Effect of Oligo A Conjugate on Virus Production

Oligo A and Oligo A Conjugate were separately dissolved in RPMI 1640 medium (ICN Biomedicals Inc., Costa Mesa, Calif.) to a final concentration of 0.2 mM (based on oligonucleotide absorbance). These stock solutions were then filtered through 0.22 μm filters to remove any possible bacterial or fungal contamination.

Monolayer of Vero cells were incubated for 1 hour at 37° C. in serum-free RPMI 1640 together with various concentrations of Oligo A or Oligo A Conjugate. The monolayers, while still exposed to oligonucleotides, were then infected with 1 plaque forming unit per cultured cell of HSV-1, strain L2 (from the Museum of Virus strains of the D.I. Ivanovskii Institute of Virology, Russian Academy of Sciences, Russian Federation). This infection method has been described by Vinogradov et al. *BBRC,* 203:959 (1994). After 8 hours of exposure to virus and oligonucleotides, the medium on the cells was replaced with fresh medium containing 10% FCS. Medium from the cells was collected at 22 and 39 hours after the ineffective incubation, and the virus titer in the collected medium was determined as described in *Virology, A Practical Approach*, Mahy, Ed., IRL Press, Oxford Univ. Press, Washington D.C. (1985). The results were as follows:

| Sample concentration (mM) | Oligonucleotide concentration (μM) | Infectious Titer of HSV-1 (PFU/ml) | |
|---|---|---|---|
| | | 22 hours post infection | 39 hours post infection |
| Control (cells without oligonucleotides) | 0 | 5x106 | 1x107 |
| Oligo A | 10 | 3x106 | 5x106 |
| | 5 | 5x106 | 1x107 |
| | 2 | 5x106 | 1x107 |
| | 1 | 5x106 | 1x107 |
| Oligo A Conjugate | 10 | 0 | 0 |
| | 5 | 0 | 5x102 |
| | 2 | 1x103 | 7x103 |
| | 1 | 5x10$^4$ | 3x10$^6$ |

EXAMPLE 18

Synthesis of a Phosphonate Monomer 40 mmoles of butanediol-1,3 (Merck) dissolved in 50 ml of anhydrous pyridine (Aldrich) were reacted with 20 mmoles 4,4'-dimethoxytritylchloride (Sigma) for 1.5 hours at 20° C. The reaction was monitored using thin layer chromatography on the silicagel plates (Merck) developed with a chloroform:methanol (95:5). The Rf of the product was 0.6. The reaction mixture was added to 200 ml of an 8% aqueous solution of the sodium bicarbonate and the product extracted with chloroform. The chloroform extract was evaporated in vacuum and the resulting oily first intermediate was used in the next stage of the synthesis.

12 mmoles of first intermediate were dissolved in 30 ml of anhydrous 1,4-dioxane, containing 3.14 ml (18 mmoles) of diisopropylethylamine (Aldrich). 18 mmoles of salicylchlorophosphite (Sigma) dissolved in 10 ml of anhydrous 1,4-dioxane were added to the diisopropyethylamine solution in small portions under an inert, argon atmosphere. The reaction mixture was incubated during 1 hour at 20° C. The reaction was monitored by the thin layer chromatography as described above. The Rf of the product was 0.05. 10 mls of water were added to the reaction mixture. After 30 min., the solvent was evaporated. The product was dissolved in 100 ml of chloroform and the solution obtained was washed stepwise with (1) 100 ml of 8% aqueous solution of the sodium bicarbonate, (2) 100 ml of 0.2 M triethyammoniumacelate solution (pH 7.2), and (3) 100 ml of water. The organic solvent was evaporated and the oily remainder, containing the phosphonate monomer was purified by chromatography on silicagel column, using stepwise gradient of (1) chloroform, (2) 3% methanol in chloroform and (3) 6% methanol in chloroform. The yield of the monomer was 4.1 g (=7.3 mmol, 63%). The product, having structure:

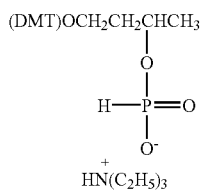

wherein DMT represents a dimethoxytrityl group, can be termed "Phosphonate Monomer A."

EXAMPLE 19

Synthesis of Polycation BDP

A 0.05 M solution of the phosphonate Monomer A in anhydrous pyridine:acetonitrile mixture (1:1) was placed in the position 6 of the DNA-synthesator (model 380-B02, Applied Biosystems, CA). A 2% solution of adamantoilchloride (Sigma) in the mixture acetonitrile:pyridine (95:5) was used as a condensing agent. The synthesis was conducted using the program modified for an H-phosphonate cycle (Sinha and Striepeke, *Oligonucleotides and Analogues: A Practical Approach*, Eckstein Ed. IRL Press, Oxford, p.185 (1991)) and the DMT-group was preserved after the synthesis was complete. Adenosine (4 μmoles) immobilized on a standard CPG-500 solid support was used as a first unit during the polymer synthesis (Vinogradov et al. *BBRC*, 203, 959 (1994). The synthesizer was programmed to add Phosphonate Monomer A repeating units to the adenosine monomer. Following all synthesis steps, the H-phosphonate groups on the immobilized substrate were oxidized with the solution of 104 mg of hexamethylenediamine (Sigma) in 0.6 ml of a mixture of anhydrous pyridine:CCl₄ (5:1) applied for 15 min. at 20° C., then the carrier was washed with the pyridine:acetonitrile mixture (1:1).

Deblocking and cap removal was achieved by ammonolysis (*Oligonucleotides and Analogues: A Practical Approach*, Eckstein Ed. IRL Press, Oxford, 1991). The product was purified by HPLC using Silasorb C., column (9×250 mm. Gilson, France) in the acetonitrile gradient (0-80%). The peak, containing dimethoxytritylated-product was collected, the solvent was evaporated and the remainder was treated with 80% acetic acid (20 min). The acetic acid was evaporated and the polycation was purified again by HPLC. The yield of the 15-mer (counted in terms of Phosphonate Monomer A) is 50% (2.2 μmoles). This created a polymer according to formula A. The polymer will be termed hereinafter "BDP."

EXAMPLE 20

Solid Phase Synthesis of the Diblock Copolymer Polyoxyethylene-BDP

Dimethoxytrityl-polyethyleneoxide-H-phosphonate was synthesized as described in Example 18 using polyethyleneglycol (1500 M.W. from Fluka) instead of butanediol-1, 3. The BDP polycation was synthesized as described in Example 19, except that, at the last stage of the chain growth, dimethoxytrityl-polyethyleneoxide-H-phosphonate was introduced as the last building block. The H-phosphonate groups of the block copolymer were oxidized as described in Example 19 using tetramethylenediamine (Sigma) instead of hexamethylenadiamine, resulting in the formation of phosphonamide bonds between the diamines and the backbone phosphates.

EXAMPLE 21

Solid Phase Synthesis of the Oligonucleotide-BDP Diblock Copolymer

A diblock copolymer comprising 12-mer oligonucleotide, 5'-GGTTCCTCCTGU (SEQ ID NO 7) (Oligo A, complementary to the splicing site of the early mRNA of type 1 Herpes Simplex Virus (HSV-1), Vinogradov et al., *BBRC*, 203:959 (1994)) and the BDP polymer was synthesized in DNA synthesator. First the BDP polymer was synthesized as described in Example 19, except that it was not removed from the support. Then the oligonucleotide chain was synthesized step-wise onto BDP polycationic polymer linked to the solid state support using the standard phosphoroamidite chemistry as described by Vinogradov et al. *BBRC*, 203, 959 (1994). The H-phosphonate groups of the diblock copolymer were oxidized as described in Example 19 using tetamethylenediamine (Sigma) instead of hexamethylenediamine.

EXAMPLE 22

Effect of Oligonucleotide-BDP Diblock Copolymer on Viral Growth

The experiment was performed exactly as described in Example 17 except that (1) the oligonucleotide-BDP copolymer of Example 21 was used and (2) a single concentration of oligonucleotide-BDP copolymer (conjugate) was used (4,4M).

| Sample | Virus titre after 39 hours |
|---|---|
| Control (without oligonucleotide) | 500 × 104 |
| Nonmodified Oligo A | 500 × 104 |
| Diblock | 5 × 104 |

EXAMPLE 23

Synthesis of Branched Polyimine Polycation

A. The polyimine polycation ("polyspermine") was obtained by stepwise polycondensation of N-(3-aminopropyl)-1,3-propanediamine and 1,4-dibromobutane as described in Example 13 and used without conjugating to poly(ethylene glycol).

B. The polyimine polycation synthesized in A was modified by dansyl chloride to obtain a fluorescent dansyl-labeled substance, purified by thin layer chromatography and a major component of the mixture (over 75% in most batches) was analyzed by electrospray mass-spectrometry in positive charge mode. The results were compared with mass-spectra obtained for the N-(3-aminopropyl)-1,3-propanediamine modified with dansyl chloride. Dansyl-labeled N-(3-aminopropyl)-1,3-propanediamine gave a four-modal peak at M+1, M+2, M+3, and M+4 (667.6, 668.5, 669.6, and 670.5). In the spectrum of the polycondensation products there were observed two types of polymodal peaks: M and M+54. For M-peaks two distinct groups were observed, with M/2H+ and M/H+, equal to 598.5 and 1195.6 respectively. This molecular mass was very close to a linear polycation with 12 nitrogen atoms (1221). M+54 peaks at 1249.8 and 652.5 correspond to a polycation with $CH_2CH_2CH_2CH_2$ crosslinks.

C. 1H-NMR spectra were obtained for the samples of the polyimine polycation synthesized in A and dissolved in DMSO. Three groups of signals were observed at 1.40-1.80 ppm (Ha), 1.80-2.20 ppm (Hb), and 2.35-2.80 ppm (Hc). Ha related to $CH_2CH_2CH_2CH_2$ protons, Hb related to $CH_2CH_2CH_2$ protons, Hc related to $—NHCH_2$ and protons. Integration of resonance signals for these three groups gave a ratio Ha:Hb:Hc equal to 1.00:0.75:1.20. The theoretical ratio for linear polycations with 12 nitrogen atoms is 1.00: 1.33:3.67. Increase in Hb:Ha and Hc:Ha ratios suggested presence of branched structures with a mixture of primary, secondary and tertiary amines.

D. The concentration of primary amino groups in the polyimine polycation synthesized in A was determined by fluorescamine method as described by Weigele et al., *J. Amer. Chem. Soc.*, 94:5927 (1972). The total amount of primary, secondary, and tertiary amino groups in the polycondensation product was determined using potentiometric titration. The ratio of the total amount of primary, secondary, and tertiary amino groups to the amount primary amino groups equals 2.7. Given the molecular masses of the condensation product determined using mass-spectrometry the result of this experiment suggests considerable branching, i.e. the presence of tertiary amines.

EXAMPLE 24

Synthesis of Linear Polyimine Polycation

Linear polycations of polyimine type are synthesized by condensation of a diaminoalkyl and bis-aldehyde in the presence of sodium cyanoborohydride using a modified reductive amination procedure described by Aziz et al., *J. Pharmac. Exper. Therapeutics*, 274:181 (1995). 0.33 g of malonaldehyde bis(dimethyl acetal) was added in 10 ml of 0.5 N HCl and stirred for 1 hour at 20° C. to obtain free bis-aldehyde. 1.27 g of N,N'-bis[3-aminopropyl]-1,4-butanediamine was added to this solution and pH was adjusted to 5.0. The mixture was allowed to stay for 1 h at 37° C., then 1.27 g of N,N'-bis[3-aminopropyl]-1,4-butanediamine was added to it and pH was adjusted to 7.0 using sodium carbonate solution. The reaction mixture was treated with 0.26 g of sodium cyanoborohydride and left for additional 1 h at 37° C. The final slightly yellow solution was desalted by gel permeation chromatography on the Sephadex G-25 column in 10% methanol and first high-molecular weight fractions revealing primary aminogroups in ninhydrine test were freeze-dried. This yielded 0.43 g of the following polyimine polycation:

EXAMPLE 25

Synthesis of Cationic Block Copolymer 1.5 g of poly(ethylene glycol), methyl ester, mw. 5000 Mw. (Sigma) was activated by 0.25 g of 1,1'-carbonyldiimidazole in 10 ml of anhydrous acetonitrile for 3 hrs at room temperature. The solvent was evaporated in vacuo, the residue redissolved in water and dialyzed through Membra-Cel MD-25-03.5 membrane with cutoff 3500 Da against water. Desalted solution was concentrated in vacuo and used in a reaction with 2-fold excess of poly-L-lysine, Mw. 4000, in methanol-water solution for 16-24 hrs at room temperature. The conjugate obtained was purified by gel-permeation column chromatography on Sephadex-50 (fine) (Pharmacia) in water and then by reverse phase chromatography on semi-preparative column (Vydac C18 5 u, 10 mm×25 cm) in acetonitrile concentration gradient. The yield was 70%. Content of aminogroups was measured by fluorescamine method and total nitrogen content was determined by elemental analysis to assess the purity of the conjugates. Usually it was about 75-90% based on graviometry.

EXAMPLE 26

Synthesis of Cationic Block Copolymer

Following the procedure of Example 25 but substituting the 2-fold excess of poly-L-lysine by the same excess of polyethyleneimine,

Mw. 2000 (Aldrich Co.), 0.4 g of the following cationic diblock copolymer is obtained:

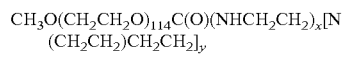

EXAMPLE 27

Synthesis of Grafted Copolymer

A. 24 g (3 mmol) of poly(ethylene glycol), mw 8000 (Aldrich Co.) were dried by co-evaporation with anhydrous pyridine in vacuo and dissolved in 50 ml of anhydrous acetonitrile. Then 0.5 μg (1.5 mmol) of 4,4'-dimethoxytrityl chloride in 30 ml of anhydrous pyridine was added to this solution dropwise under continuous stirring during 30 min. The mixture was allowed to stand for additional 2 h at room temperature, then the solvents were evaporated in vacuo. The residue was dissolved in 50 ml of dichloromethane, extracted with 5% sodium bicarbonate (2×30 ml), and applied on the Silicagel column (3×45 cm, 40-60 μm). Stepwise elution with dichloromethane-methanol solutions separated a slightly yellow mono-4,4'-dimethoxytrityl-derivative of poly(ethylene glycol) with an yield about 75-85%. The side product of the reaction (10-15% yield) was the bis-4,4'-dimethoxytrityl-derivative of poly(ethylene glycol).

B. 1.5 g of mono-4,4'-dimethoxytrityl-derivative of poly (ethylene glycol) obtained in A was activated by 0.25 g of 1,1'-carbonyidiimidazole in 10 ml of anhydrous acetonitrile for 3 hrs at room temperature. The solvent was evaporated in vacuo, the residue redissolved in water and dialyzed through Membra-Cel MD-25-03.5 membrane with cutoff 3500 Da against water. Desalted solution was concentrated in vacuo and then reacted with poly-L-lysine, Mw. 19000 in methanol-water solution for 24 h at room temperature at a molar ratio of poly(ethylene glycol) to free aminogroups of poly-L-lysine 0.7:1.0. The conjugate obtained was purified by gel-permeation column chromatography on Sephadex-50 (fine) (Pharmacia) in water and then by reverse phase chromatography on semi-preparative column (Vydac C18 5 u, 10 mm×25 cm) in acetonitrile concentration gradient. This yields a grafted polylysine copolymer at 35% yield in which 50% of free aminogroups are substituted with poly (ethylene glycol) as determined by fluorescamine method.

EXAMPLE 28

Synthesis of Grafted Copolymer

A. 24 g (3 mmol) of poly(ethylene glycol), mw 8000 (Aldrich Co.) were dried by co-evaporation with anhydrous pyridine in vacuo and dissolved in 50 ml of anhydrous acetonitrile. Then 0.5 µg (1.5 mmol) of 4,4'-dimethoxytrityl chloride in 30 ml of anhydrous pyridine was added to this solution dropwise under continuous stirring during 30 min. The mixture was allowed to stand for additional 2 h at room temperature, then the solvents were evaporated in vacuo. The residue was dissolved in 50 ml of dichloromethane, extracted with 5% sodium bicarbonate (2×30 ml), and applied on the Silicagel column (3×45 cm, 40-60 µm). Stepwise elution with dichloromethane-methanol solutions separated a slightly yellow mono-4,4'-dimethoxytrityl-derivative of poly(ethylene glycol) with an yield about 75-85%. The side product of the reaction (10-15% yield) was the bis-4,4'-dimethoxytrityl-derivative of poly(ethylene glycol).

B. 1.5 g of mono-4,4'-dimethoxytrityl-derivative of poly (ethylene glycol) obtained in A was activated by 0.25 g of 1,1'-carbonyldiimidazole in 10 ml of anhydrous acetonitrile for 3 hrs at room temperature. The solvent was evaporated in vacuo, the residue redissolved in water and dialyzed through Membra-Cel MD-25-03.5 membrane with cutoff 3500 Da against water. Desalted solution was concentrated in vacuo and then reacted with polyethyleneimine, Mw. 25,000 in methanol-water solution for 24 h at room temperature at a molar ratio of poly(ethylene glycol) to free aminogroups of polyethyleneimine 0.7:1.0. The conjugate obtained was purified by gel-permeation column chromatography on Sephadex-50 (fine) (Pharmacia) in water and then by reverse phase chromatography on semi-preparative column (Vydac C185 µm, 10 mm×25 cm) in acetonitrile concentration gradient. This yields a grafted polyethyleneimine block copolymer at 85% in which 45% of free aminogroups are substituted with poly(ethylene glycol) as determined by fluorescamine method as described by Weigele et al. (*J. Amer. Chem. Soc.*, 1972, 94:5927).

EXAMPLE 29

Synthesis of Grafted Copolymer

Following the procedure of Example 28 but using a molar ratio of activated poly(ethylene glycol) to free aminogroups of polyethyleneimine 0.3:1.0, there is obtained in 80% yield a grafted polyethyleneimine copolymer in which 24% of free aminogroups are substituted with poly(ethylene glycol).

EXAMPLE 30

Synthesis of Cationic Block Copolymer

Following the procedure of Example 26 but substituting 6.0 g of polyethyleneglycol, mw 20,000 for the excess of polyethylene glycol, mw 5,000 there is obtained 6.0 g of the cationic block copolymer:

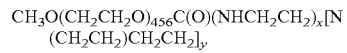

EXAMPLE 31

Synthesis of Cationic Block Copolymer

A. Following the procedure of Example 26 but substituting 1.5 g of polyethyleneglycol, Mw. 5,000 by 2.4 g of polyethyleneglycol, Mw. 5,000 (Aldrich Co.) there is obtained 1.2 g of the cationic block copolymer containing polyethyleneinmine and polyethyleneglycol chain segments.

B. The molecular mass of this block-copolymer was determined by static light scattering method using DAWN multi-angle laser photometer (Wyatt Technology, Santa Barbara, Calif.) which operated at 15 angles and equipped with He-Ne laser (632.8 nm). The samples of the block copolymer were dialyzed through membrane with cutoff 3,500 Da against $4.5 \times 10^{-3}$ g/ml NaCl and then filtered directly into flow cell used for light scattering experiments. Weigh-average molecular mass was calculated on the base of four measurements. Cell constant was determined by calibration with different concentrations of NaCl. Specific refractive index increment (dn/dc) was measured using Wyatt/Optilab 903 interferometric refractometer at 632.8 nm. The molecular mass of the sample obtained was 16,000, suggesting that this polymer contained approximately one polyethyleneinmine segment and two polyethyleneglycol segments.

C. The number of the primary aminogroups in the synthesized sample of the copolymer was determined using a modified procedure described by Weigele et al. (*J. Amer. Chem. Soc.*, 1972, 94:5927). To 1.5 ml of a sample in 20 mM sodium borate, pH 9.5 (aminogroups concentration up to 100 µM) 0.25 ml of fluorescamine solution (0.024%, Sigma) in acetone was added and vortexed for 5 min. The measurements have been made on Shimadzu spectrofluorometer at excitation wavelength 384 nm and at 430 to 510 nm emission wavelength range. Extinction coefficient at emission 475 nm was determined as equal to $1.58 \times 10^6$ M$^{-1}$. The specific amount of primary aminogroups was 0.69 mmol/g.

EXAMPLE 32

Synthesis of Grafted Copolymer

Following the procedure of Example 28 but substituting 24 g of poly(ethylene glycol) by the same amount of Pluronic L61 (BASF Co.) and using a molar ratio of activated Pluronic L61 to free aminogroups of polyethyleneimine 0.3:1.0, there is obtained in 22% yield a grafted polyethyleneimine copolymer in which 8% of free aminogroups are substituted with Pluronic L61.

EXAMPLE 33

Synthesis of Grafted Copolymer

Following the procedure of Example 28 but substituting 24 g of poly(ethylene glycol), by the same amount of Pluronic P85 and using a molar ratio of activated Pluronic P85 to free aminogroups of polyethyleneimine 0.3:1.0 there is obtained in 70% yield a grafted polyethyleneimine copolymer in which 11% of free aminogroups of polyethyleneimine are substituted with Pluronic P85.

EXAMPLE 34

Synthesis of Grafted Copolymer

Following the procedure of Example 28 but substituting 24 g of poly(ethylene glycol), by the same amount of Pluronic P123 (BASF Co.) and using a molar ratio of activated Pluronic P123 to free aminogroups of polyethyleneimine 0.3:1.0 there is obtained in 30% yield a grafted polylysine copolymer in which 9% of free aminogroups are substituted with Pluronic P123.

EXAMPLE 35

Synthesis of Grafted Copolymer

Following the procedure of Example 28 but substituting 24 g of poly(ethylene glycol), by the same amount of Pluronic F38 (BASF Co.) and using a molar ratio of activated Pluronic F38 to free aminogroups of polyethyleneimine 0.3:1.0 there is obtained in 40% yield a grafted polylysine copolymer in which 9% of free aminogroups are substituted with Pluronic F38.

EXAMPLE 36

Synthesis of Multi-grafted Copolymer

Following the procedure of Example 28 but substituting polyethyleneimine by polyethyleneimine modified with Pluronic L123 (BASF Co.) obtained in Example 35 and using a molar ratio of activated poly(ethylene glycol) to free aminogroups of modified polyethyleneimine 0.4:1.0 there is obtained in 20% yield a grafted polyethyleneimine copolymer in which 9% of free aminogroups are substituted with Pluronic L123 and 30% of groups are substituted with poly(ethylene glycol).

EXAMPLE 37

Complex with Oligonucleotide

A. Model phosphorothioate oligodeoxyribonucleotide PS-dT20 was synthesized using ABI 291 DNA Synthesizer (Applied Biosystems, San Diego, Calif.) following the standard protocols. After ammonia deprotection the oligonucleotide was twice precipitated by ethanol and then used without purification.

B. The complex formed between the PS-dT20 and polyethyleneimine-poly(ethylene glycol) block copolymer obtained in Example 28 was obtained by mixing the aqueous solutions of these polymers in 10 mM phosphate buffer, pH 7.4 so that the ratio of the primary amino groups of the block copolymer to the phosphate charges of the PS-dT20 was 1.0. All solutions were prepared using double distilled water and were filtered repeatedly through the Millipore membrane with pore size 0.22 μM.

C. The electrophoretic mobility (EPM) and the size of the particles of the complex synthesized in B were determine. The EPM measurements were performed at 25° C. with an electrical field strength of 15-18 V/cm using "ZetaPlus" Zeta Potential Analyzer (Brookhaven Instrument Co.) with 15 mV solid state laser operated at a laser wavelength of 635 nm. The zeta-potential of the particles was calculated from the EPM values using the Smoluchowski equation. Effective hydrodynamic diameter was measured by photon correlation spectroscopy using the same instrument equipped with the Multi Angle Option. The sizing measurements were performed at 25° C. at an angle of 90°. The zeta potential of this sample was close to zero, suggesting that particles were electroneutral. The average diameter of the particles was 35 nm.

EXAMPLE 38

Stability Against Nuclease Digestion

100 μg of the complex formed between the PS-dT20 and polyethyleneimine-poly(ethylene glycol) block copolymer obtained in Example 39 was treated by 1 mg of snake venom phosphodiesterase (Phosphodiesterase I from *Crotalus adamanteus,* 0.024 units/mg, Sigma) for 2 and 18 hrs at 37° C. Reaction mixtures were analyzed by gel permeation HPLC for digested PS-dT20. The digestion of the PS-dT20 in this complex was less than 5%. In contrast, free PS-dT20 treated with the same concentration of enzyme for the same time interval was digested completely.

EXAMPLE 39

Accumulation of Oligonucleotide in Caco-2 Monolayers

A. A 5'-aminohexyl PS-dT20 oligonucleotide was synthesized using ABI 291 DNA Synthesizer (Applied Biosystems, San Diego, Calif.) following the standard protocols. After ammonia deprotection the oligonucleotide was twice precipitated by ethanol and then used without purification. 5'-Aminohexyl PS-dT20 was labeled by reaction with fluorescein isothiocyanate (Sigma) following the manufacturer protocol. Fluorescein-labeled PS-ODN was separated from unreacted fluorophore using a Pharmacia PD-10 size exclusion.

B. The complex formed between the fluorescein-labeled PS-dT20 and polyethyleneimine-poly(ethylene glycol) block copolymer was synthesized as described in Example 37 but using fluorescein-labeled PS-dT20 instead of PS-dT20.

C. Caco-2 cells, originating from a human colorectal carcinoma (Fogh et al. J. Natl. Cancer Inst., 59:221-226, 1977) were kindly provided by R. T. Borchardt (The University of Kansas, Lawrence, Kans.). The cells were maintained in Dulbecco's Modified Eagle's Medium (DMEM), containing 10% heat-inactivated fetal bovine serum (FBS), 1% non-essential amino acids, benzylpenicilin (100 μ/ml) and streptomycin (10 μg/ml), in an atmosphere of 90% air and 10% $CO_2$ as described by Artursson (*J. Pharm. Sci.,*

79:476-482, 1990). All tissue culture media were obtained from Gibco Life Technologies, Inc. (Grand Island, N.Y.). The cells were grown on collagen coated polycarbonate filter chamber inserts (Transwell, Costar Brand Tissue Culture Products, Contd.; pore size 0.4 μm; diameter 24.5 mm). 250,000 cells were added to each insert and cells of passage number 32-45 were used. The cells were fed every second day and were allowed to grow and differentiate for up to 14 days before the monolayers were used in the following absorbtion experiments.

D. Caco-2 cell monolayers were preincubated for 30 min. at 37° C. with assay buffer, containing sodium chloride (122 mM), sodium bicarbonate (25 mM), glucose (10 mM), HEPES (10 mM), potassium chloride (3 mM), magnesium sulfate (1.2 mM), calcium chloride (1.4 mM) and potassium phosphate dibasic (0.4 mM). After this, the assay buffer was removed and the cells were exposed to 50 μM fluorescein-labeled PS-ODN or its complex in the assay buffer for 90 min. at 37° C. After that the dye solutions were removed and cell monolayers were washed three times with ice-cold PBS. Cells were then solubilized in 1.0% Triton X-100 and aliquots (25 μl) were removed for determination of cellular fluorescence using a Shimadzu RF5000 spectrofluorometer at $\lambda ex=488$ nm, $\lambda em=520$ nm. Samples were also taken for protein determination using the Pierce BCA method.

The amounts of fluorescein-labeled PS-dT20 absorbed by the cells was as follows:

| Sample | Cellular accumulation of oligonucleotide, nmol/mg protein |
|---|---|
| Free fluorescein-labeled PS-dT20 | 0.14 ± 0.03 |
| The complex | 0.5 ± 0.01 |

This demonstrates that incorporation of polynucleotide in the complex with the block copolymer increases cellular accumulation of polynucleotide by more than 3-times.

EXAMPLE 40

Transport of Oligonucleotide Across Caco-2 Monolayers

A. The filter-grown Caco-2 monolayers were used for oligonucleotide permeability studies after complete maturation, i.e., as from day 14 after plating. Filters were gently detached from the wells and placed in Side-Bi-Side diffusion cells from Crown Bio. Scientific, Inc. (Somerville, N.J.) maintained at 37° C.±0.1° C. This system is used as an in vitro model of human intestinal epithelium to evaluate oral bioavailability of drugs (Pauletti et al., *Pharm. Res.*, 14:11-17 (1977). Cell monolayers were preincubated for 30 minutes at 37° C. with the assay buffer, containing 10% heat-inactivated fetal bovine serum (FBS), 1% non-essential amino acids, benzylpenicilin (100 μ/ml) and streptomycin (10 μg/ml), added to both donor and receptor chambers (3 ml). After preincubation, the assay buffer in the receptor container was replaced by the fresh one, while the assay buffer in the donor container was replaced by 50 μM fluorescein-labeled PS-ODN or its complex in the assay buffer. To account for the integrity of the monolayers the R123 solutions in the donor container also contained $H^3$-labeled manitol, a paracellular marker (Dawson, *J. Membrane Biol.*, 77:213-233 (1977) obtained from DuPont Corp. (Boston, Mass.). At 120 min., the solutions in the receptor chamber were removed for determination of fluorescein-labeled PS-ODN using a Shimadzu RF5000 fluorescent spectrophotometer ($\lambda ex=488$ nm, $\lambda em=520$ nm) and $H^3$-manitol determination using a liquid scintillation counter (Hewlett Packard Instruments). Immediately after collecting the solutions in the receptor chamber 3 ml of fresh assay buffer was added to this chamber. The transport of fluorescein-labeled PS-ODN (or manitol) across Caco-2 cell monolayers was expressed as a percentage of the total fluorescein-labeled PS-ODN (or manitol) accumulated in the receptor chamber to the initial amounts of fluorescein-labeled PS-ODN (or manitol) in the donor chamber. A minimum of three different membranes was studied for each drug composition at multiple time points for each membrane. The results were as follows:

| Sample | PS-dT20 transport, % | Manitol transport, % |
|---|---|---|
| Free fluorescein-labeled PS-dT20 | 0.001 ± 0.0005 | 4.0 ± 0.1 |
| The complex | 0.075 ± 0.005 | 4.2 ± 0.02 |

This demonstrates that incorporation of polynucleotide in the complex with the block copolymer increases transport of this polynucleotide across Caco-2 monolayers by more than 7-times while the transport of paracellular marker is not affected.

EXAMPLE 41

In Vitro Transfection of Plasmid DNA with Various Block Copolymers-based Formulations These experiments are performed in Cos-7 cells and carried out as follows; Cos-7 cells are used and are seeded at $7 \times 10^5$ per well in 12-well plate (Costar) and allowed to rest 24 hours before transfection (confluenly at 70%). Three μg of pGL3-Luc SV40 is formulated with the different polymers at various N/P ratios. The transfection mixture is prepared as follows; to an eppendorf tube containing 100 μl of DMEM supplemented with 1% Hepes the following is added; 30 μl of DNA at 0.1 mg/ml, 35 μl of polymer to be tested at various concentrations to get a variety of N/P ratios. The transfection mixture is allowed to incubate 5 minutes before completing to 1 ml with complete DMEM (10% FBS, 1% Hepes, 1% penicillin-streptomycin). Five hundred l of the transfection mixture is added per well. Following a 4-hours transfection at 37° C. and under a 5% CO2 atmosphere, the cells are rinsed with PBS and allowed to rest overnight in 1 ml of complete DMEM before being harvested to perform the luciferase assay according to Promega Corporation's recommendation. Briefly, the cells are lysed on ice for 30 minutes and then centrifuged at 13,000 g for 2 minutes. The supernatents are kept and analyzed for luciferase activity. The assay is performed as follows: 20 l of supernatent is added to luminometric tubes containing 100 l of luciferase substrate. Light emission is measured with a luminometer (Berthold) for a period of 5 seconds. The data is reported in relative light units per second and normalized for proteins with the BiCinchoninic Acid assay kit (Sigma). The results show that pluronic P123 conjugated to PEI improves transfection of CMV-Luc compared to PEI alone suggesting that the block copolymer moiety is advantageous for a better transfection. Note that P123 alone does not transfect cells and is totally inefficient like CMV-Luc alone.

This observation is in contrast to the data shown in example 44 where P123 is used to improve gene expression in muscle.

| Transfection mixture | Luciferase signal (RLU/s/ug proteins) |
|---|---|
| CMV-Luc alone | 15 ± 4 |
| CMV-Luc + P123-PEI/P123 | 1789456 ± 45789 |
| CMV-Luc + P123 | 26 ± 6 |
| CMV-Luc + PEI | 678543 ± 32591 |

EXAMPLE 42

Block Copolymers as Biological-modifiers of DNA Biodistribution

CMV-Luc (50 μg) or oligonucleotides (100 μg) are resuspended in a volume of 200 ul containing various block copolymers-based formulations and injected i.v. into C57Bl/6 (6-8 week-old) female mice. Twenty-four hours following the injection the mice are sacrificed to harvest various organs in which luciferase activity is measured or in which oligonucleotide accumulation is determined. For plasmid DNA, all major organs are rapidly homogenized with a tissue grinder (Kontes Glass Co.) in cell lysis buffer (Promega Corporation) supplemented with protease inhibitors. The extraction mixture is kept on ice for 30 minutes and then centrifuged at a maximum speed for 2 minutes. The supernatents are kept and analyzed for luciferase activity. The assay is done as follows: 20 μl of supernatent is added to luminometric tubes containing 100 μl of luciferase substrate (Promega Corporation). Light emission is measured with a luminometer (Berthold) for a period of 5 seconds. The data is reported in pg of luciferase per mg of proteins. For oligonucleotides, the major organs are extracted twice with phenol:chloroform and precipitated with ethanol before quantification. The results show that with conventional liposomal formulation and PEI that gene expression is concentrated in the lungs which is a factor known to increase risks of pulmonary embolism. However, gene expression is redirected to liver when formulated with PEI conjugated to a hydrophobic block copolymer such as P123. In addition, when P123 is used alone, gene expression in various organs is very low except in muscle tissue. For oligonucleotides, the accumulation is observed is kidneys when a hydrophobic carrier (PEI conjugated to PEG) is used and is redirected to liver when a hydrophobic carrier (P85-PEI/P85) is used. Various and a multitude of mixture of block polymers can be prepared to give a wide range of hydrophobic and hydrophylic balances that can redirect gene expression and oligonucleotides accumulation in various regions of the body.

| Transfection mixture | Organs with the highest luciferase signal or with the highest accumulation of oligonucleotides |
|---|---|
| CMV-Luc alone | none |
| CMV-Luc + P123-PEI/P123 | Liver |
| CMV-Luc + P123 | Muscle |
| CMV-Luc + PEI | Lungs |
| CMV-Luc + Liposome (Dotap-chol) | Lungs |
| Oligo alone | Lungs and Liver |
| Oligo + PEI conjugated to PEG | Kidneys |
| Oligo + P85-PEI/P85 | Liver |

EXAMPLE 43

Intramuscular Transfection with Block Copolymers

In this experiment, block copolymers are used to improve gene expression in muscle (tibialis anterior) of C57Bl/6 (6-7 week-old) female mice kept by groups of 4 and fed ad libidum. Five μg of CMV-driven plasmid DNA encoding for luciferase is formulated with block copolymers and injected i.m. into the tibialis anterior muscle. Before each intramuscular injection, the mice are anesthetized with a mixed solution of ketamine and xylazine. Mice are sacrificed 5 days following the i.m. injection and each injected muscle is dissected and rapidly homogenized with a tissue grinder (Kontes Glass Co.) in cell lysis buffer (Promega Corporation) supplemented with protease inhibitors. The extraction mixture is kept on ice for 30 minutes and then centrifuged at a maximum speed for 2 minutes. The supernatents are kept and analyzed for luciferase activity. The assay is done as follows: 20 μl of supernatent is added to luminometric tubes containing 100 μl of luciferase substrate (Promega Corporation). Light emission is measured with a luminometer (Berthold) for a period of 5 seconds. The data is reported in relative light units per second per tibialis anterior. As shown in the table below, block copolymers improve gene expression measured after 5 days post-injection. The use of a cationic reagent does not improve but inhibited gene expression. The reason of this improvement may lie in the block copolymer's property of changing the surface tension of muscle cells and thus increasing the uptake of plasmid DNA in myotubes.

| Treatment applied to tibialis anterior (TA) | Relative light units/second/TA | Fold-increase |
|---|---|---|
| Naked DNA (n = 26) | 31104 ± 1404 | — |
| Block copolymer formulated DNA (n = 18) | 205448 ± 17950 | 6.6× |
| Cationic reagents (n = 4) | 15 ± 3 | — |

EXAMPLE 44

Concentration of Block Copolymers Improving Gene Expression in Muscle

These experiments are carried out like in example 43 except that the concentration of block copolymers used for the i.m. injection is titrated. The concentrations of block copolymers used to perform intramuscular delivery of plasmid DNA are low. The concentrations of block copolymers used for intramuscular injection do not form gels. The solutions of block polymers consist in micelles and unimers of block polymers. The concentrations improving intramuscular gene expression are lower than 0.1% as shown below with the arrow. This concentration is about 100 times lower than the Maximal Tolerable Dose when the same block copolymers are injected I.V. Also, some combination of block copolymers can even improve further gene expression.

| PLURONIC P123 | |
|---|---|
| P123 (%) | RLU/s/T.A. muscle |
| 0 | 31005 ± 5619 |
| 0.0007 | 6052 ± 1778 |
| 0.007 | 100499 ± 30455 |
| 0.07 | => 130113 ± 46871 |
| 0.7 | 5368 ± 1505 |
| 7 | 160 ± 23 |

| COMBINATION OF PLURONIC F127/L61 | |
|---|---|
| F127/L61 (%) | RLU/s/T.A. muscle |
| 0 | 62565 ± 7569 |
| 0.01 | => 564397 ± 53813 |
| 0.05 | 500 584 ± 40491 |
| 0.1 | 299 050 ± 29592 |

EXAMPLE 45

Prolongation of Gene Expression with Block Copolymers

In this experiment, plasmid DNA encoding for luciferase is formulated with block copolymers like in example 43 except that the muscles are harvested after 48 hours and 2 weeks. As shown in the table below gene expression is prolonged with block copolymers.

| | After 48 hours (RLU/s/T.A. muscle) | After 2 weeks (RLU/s/T.A. muscle) |
|---|---|---|
| Naked DNA (n = 6) | 17143 ± 2886 | 1389 ± 405 |
| Block copolymer formulated DNA (n = 18) | 54377 ± 12486 | 20121 ± 7934 |

EXAMPLE 46

Kinetics of Gene Expression in Muscle with Block Copolymers

The kinetic experiments are prepared in conditions like that described in example 43 except that the muscles are harvested at day 1, 2, 3, 4, and 7. As shown the table below gene expression starts earlier with block copolymers and remain the same over a period of 7 days.

| Day | Naked DNA (RLU/s/T.A. muscle) | DNA formulated with block copolymers (RLU/s/T.A. muscle) |
|---|---|---|
| 1 | 93419 ± 10835 | 526902 ± 39724 |
| 2 | 141705 ± 8293 | 722485 ± 43789 |
| 3 | 59663 ± 5558 | 311470 ± 20066 |
| 4 | 786200 ± 77419 | 1295196 ± 82725 |
| 7 | 168350 ± 11103 | 1202503 ± 108929 |

EXAMPLE 47

Cross-species Comparison of Intramuscular Gene Expression

Block copolymers are used to formulate plasmid DNA like in example 43 but injected to 2 different species, mice and rats. Tibialis anterior of 6-8 weeks old mice and 3 months old rats are harvested 48 hours following the intramuscular injection. Two assumptions can be drawn from the table shown below; (1) block copolymers can be applied to more than one species and likely to be applicable to other species like humans, and (2) block copolymers promote gene expression in older animal suggesting that block copolymers are likely to facilitate the transfection of mature myofibers.

| | 6–8 week old mice (RLU/s/T.A. muscle) | 3 month old rats (RLU/s/T.A. muscle) |
|---|---|---|
| Naked DNA | 17143 ± 2886 | 2749 ± 839 |
| Block copolymer-formulated DNA | 54377 ± 12486 | 70504 ± 8483 |

EXAMPLE 47A

Conjugation of PLURONIC® F127 and Spermine

PLURONIC® F127 conjugated to spermine is obtained by following the procedure of example 28 but substituting 24 g of poly (ethylene glycol) by the same amount of PLURONIC® F127 (BASF Co.) and substituting polyethyleneimine, M.W. 25,000 by spermine (Sigma-Aldrich, St-Louis) and using molar excess of 10 g of spermine per 10 g of poly (ethylene glycol) activated by 1,1'-carbonyldiimidazole. This method produced 15 g of spermine conjugated PLURONIC® F127.

EXAMPLE 47B

Intramuscular Transfection with Block Copolymer Conjugated to Spermine

In this example PLURONIC® F127 was conjugated to spermine as described in example 47A and used to transfect plasmid DNA into the tibialis anterior of 6-8 weeks old C57Bl/6 mice. Mice were kept by groups of 5 and fed ad libidum. Five ug of CMV-driven plasmid DNA encoding luciferase is formulated with F127 conjugated to spermine and injected into the tibialis anterior muscles. The rest of the protocol is as in Example 43. The data are shown in the table below. The data demonstrate that spermine conjugated to F127 and formulated with DNA increase transgene expression compared to naked DNA.

| Treatment applied to tibialis anterior (TA) | Relative light units/second/TA | Fold-increase |
|---|---|---|
| Naked DNA (n = 6) | 292825 ± 32596 | — |
| F127-spermine 0.02% (n = 6) | 2217817 ± 109632 | 7.6× |

EXAMPLE 47

Intramuscular Transfection Using Block Copolymer Mixed with Spermine

In this example PLURONIC® F127 was mixed to spermine and used to transfect plasmid DNA into the tibialis anterior of 6-8 weeks old C57Bl/6 mice. Mice were kept by groups of 5 and fed ad libidum. Five ug of CMV-driven plasmid DNA encoding luciferase is formulated with F127 mixed to spermine and injected into the tibialis anterior muscles. The rest of the protocol is as in Example 43. The data are shown in the table below. The data demmonstrate that spermine mixed with Pluronic block copolymer increases the rate of transfection.

| Treatment applied to tibialis anterior (TA) | Relative light units/second/TA | Fold-increase |
|---|---|---|
| Naked DNA (n = 6) | 949966 ± 56286 | — |
| F127 (0.02%) + spermine (2:1 molar ratio) (n = 6) | 1936409 ± 78265 | 2.0× |

EXAMPLE 48

Treatment of Ischemic Tissues with Block Copolymers

Ten days after ischemia is induced in one rabbit hindlimb, 500 g of phVEGF165 (or any other DNA plasmid encoding for growth factors known to with 0.1% w/v of block copolymers is injected I.M. into the ischemic hindlimb muscles (Tsurumi Y. et al., *Circulation*, 94:12, 3281-90 (1996)). Thirty days later, an angiography is performed to recognize collateral vessels and histology analyses are carried out to identify capillaries. Ischemic skeletal muscle represents a promising target for gene therapy with naked plasmid DNA formulated with block copolymers. I.M. transfection of genes encoding angiogenic cytokines, particularly those that are naturally secreted by intact cells, may constitute an alternative treatment strategy for patients with extensive peripheral vascular disease.

EXAMPLE 49

Block Copolymers Used for Gene-based Vaccination

Block copolymers could be used to raise any humoral and cellular immune response against various antigens associated with diseases (cancer, viral infection, etc.). The following example focuses but not limited to HIV. A block copolymer formulation containing a plasmid DNA construct consisting in gp120 gene of HIV, driven by a cytomegalovirus (CMV) promoter is prepared. A volume of 50 µl of a block copolymer formulation is prepared containing 5 µg of gp120 plasmid DNA and 0.01% of block copolymer is injected into the tibialis anterior muscle. At about 2 weeks after injection, the muscle is removed from the injection site, and prepared as a cell lysate according to the procedures of example 41 to detect the presence of gp120 by means of ELISA kits (Abbot Labs, Chicago, Ill.). The ability of gp120 antibody present in serum of the plasmid DNA vaccinated mice to protect against HIV infection is determined by a HT4-6C plaque reduction assay, as follows: HT4-6C cells (CD4$^+$ HeLa cells) are grown in culture in RPMI media (BRL, Gaithersburg, Md.). The group of cells is then divided into batches. Some of the batches are infected with HIV by adding approximately $10^5$ to $10^6$ infectious units of HIV to approximately $10^7$ HT4-6C cells. Other batches are tested for the protective effect of gp120 immune serum against HIV infection by adding both the HIV and approximately 50 µl of serum from a mouse vaccinated with gp120 plasmid DNA. After 3 days of incubation, the cells of all batches are washed, fixed and stained with crystal violet, and the number of plaques counted. The protective effect of gp120 immune serum is determined as the reduction in the number of plaques in the batches of cells treated with both gp120 plasmid DNA-vaccinated mouse serum and HIV compared to the number in batches treated with HIV alone.

EXAMPLE 50

Functional Expression of Dystrophin in Dystrophic Mouse Muscle in Vivo

A plasmid containing the dystrophin gene under control of the Rous Sarcoma virus promoter is prepared from the Xp21 plasmid containing the complete dystrophin coding region and the SV40 poly. 200 µg of the plasmid in 100 µl of Dystrophin abnormalities of Duchenne's/Becher Muscular 0.1% block copolymers solution is injected into the quadriceps the mutant mouse strain lacking the dystrophin gene product (MDX mouse; Jackson labs). Expression of functional dystrophin is monitored 7 days post injection by immunohistochemistry according to the procedures described by Watkins et al. and using the same anti-dystrophin antibody (anti-60 kd antibody with a fluorescent secondary antibody). Functional expression of the dystrophin gene product in the dystrophic mice is detected by comparing the pattern of fluorescence observed in cross-sections of quadriceps muscle from injected animals, with the fluorescence pattern observed in normal animals. Watkins S. C., Hoffman E. P., Slayter H. S., Kinkel L. M., Immunoelectron microscopic localization of dystrophin in myofibres, *Nature*, Jun. 30, 1988; 333 (6176:863-6). Normal dystrophin expression is localized underneath the plasma membrane of the muscle fiber, so that a cross section of the quadriceps muscle give a fluorescence pattern encircling the cell. In addition dystrophin expression is quantitated by Western blot analysis using the affinity purified anti-60 kd antibody.

EXAMPLE 51

A Combination of Block Copolymers Improves Gene Expression Following Intradermal Administration In this experiment, block copolymers are used to improve gene expression in the skin of C57B1/57 (6-7 week-old) female mice kept by groups of 5 and fed ad libidum. Five ug of plasmid pCMV-Luc was formulated with 50 ul of a solution containing a combination of the block copolymers PLURONIC® F127/L61. Plasmid pCMV-Luc was a gift from Dr. Albert Descoteaux from the University of Quebec, INRS-IAF. The block copolymers were in a w:w ratio of 8:1 (F127:L61) at a final concentration of 0.01%W:V. The formulation was injected at the tail base of at least 5 C57Bl/57 mice. Seven days later the skin and tissue surrounding the injection site was collected and extracted to monitor the luciferase activity as in Example 42. Luciferase activity was measured as described in Example 42. The following data were obtained and activity levels were compared to those of control mice that received only naked DNA in saline.

The results demonstrate that plasmid DNA formulated with a combination of block_copolymers exhibited 20-fold higher levels of Luciferase gene expression than DNA administered without the block copolymer.

EXAMPLE 52

A Combination of Block Copolymers Improves the Humoral Immune Response to DNA Compositions Injected Intradermally In this experiment, block copolymers are used to improve the humoral immune response to the protein encoded by a DNA molecule injected intradermally into C57Bl/57 mice (6-7 week-old) female mice kept by groups of 5 and fed ad libitum. The C57Bl/57 mice were injected intradermally with 5 ug of pCMV-Bgal (enclloding the β-galactosidase protein) with or without a combination of block copolymers of PLURONIC® F127/L61. The formulation was prepared as described in Example 51. Blood samples were collected 2 and 4 weeks after injection to monitor the humoral immune response specific to β-galactosidase. The detection of specific anti-p-galactosidase antibodies was determined by means of an ELISA.

The ELISA was performed by allowing the adsortion of β-galactosidase in 96-well plates overnight. Before the addition of a series of diluted sera, the plates were blocked for 2 hours with PBS-BSA 1%. Following an incubation of 1 hour, the sera were discarded, the plates rinsed twice with PBS-Tween 0.01% and the secondary antibodies (anti-mouse IgG conjugated to horse raddish peroxidase) added to the plate. Prior to the addition of the ABTS substrate, the plate was rinsed twice with PBS-TWEEN® 0.01%.

The data are expressed as the percentage of mice responding to the 26 antigen and the average titers of the responding mice. None of the mice injected with non-formulated pCMV-Bgal responded to the antigen. However, 2 and 4 weeks after inoculation, 33% and 66%, respectively, of the mice injected with pCMV-Bgal formulated with a combination of block copolymers responded. This example demonstrates that block copolymers enhance the immune response to a protein encoded by a plasmid.

| Formulation | Percentage of responders(Average titers) | |
| --- | --- | --- |
| | 2 weeks | 4 weeks |
| PCMV-Bgal | 0 | 0 |
| PCMV-Bgal + PLURONIC ® F127/L61 | 33(1:2000) | 66(1:2000) |

EXAMPLE 53

A Combination of Block Copolymers Improved the Humoral Immune Response Against a Protective Surface Antigen (ORF5) of the Porcine Reproductive and Respiratory Syndrome Virus (PRRSV)

In this experiment, the plasmid pCMV-ORF5 formulated with a combination of block copolymers and injected intradermally improved the immune response to the encoded protein. Balb/C mice (6-7 week-old) and kept in groups of 4_were injected intradermally with 5 ug of the plasmid pCMV-ORF5 (encoding the GP5 protein) with or without a combination of block copolymers. The formulation was prepared as described in Example 51. Blood samples were collected 3 and 5 weeks after inoculation to monitor the humoral immune response specific to GP5. A booster inoculation was given after the first 3 week blood collection.

The results demonstrate that mice injected with pCMV-ORF5 formulated with a combination of block copolymers developed a stronger humoral immune response than mice that received the plasmid DNA alone as shown by the increased average titer of anti-GP5 antibodies.

| Formulation | Average titers post-immunization | |
| --- | --- | --- |
| | 3 weeks | 5 weeks |
| pCMV-ORF5 alone | 0 | 1:100 |
| pCMV-ORF5 + PLURONIC ® F127/L61 | 1:80 | 1:600 |

EXAMPLE 54

A Single Block Copolymer Improves the Humoral Immune Response to DNA Compositions Administered Intradermally In this experiment, C57Bl/57 mice (6-8 week old and 6 mice per sample set) were injected intradermally with 5 or 50 ug of pCMV-Bgal with and without PLURONIC® 85 at a final concentrations of 0.1% or 0.01. Blood samples were collected 2 and 4 weeks after inoculation to monitor the humoral immune response specific to β-galactosidase. The detection of specific anti-β-galactosidase antibodies was determined by an ELISA as in Example 52.

The data are expressed as the percentage of mice responding to β-galactosidase and the average titers of the anti-13-galactosidase antibodies in the responding mice. The results demonstrate that fewer mice injected with the non-formulated pCMV-Bgal showed a response to the 62 -galactosidase than those mice injected with pCMV-Bgal formulated with PLURONIC®_P85. This difference occurred in mice receiving either concentration of plasmid DNA. Also, the titers were higher in the mice injected with pCMV-Bgal formulated with PLURONIC®P85 than the mice that received the non-formulated pCMV-Bgal. A weaker response with PLURONIC P85 at a concentration of 0.1% is likely due to lower gene expression. P85 at 0.01% is a more optimal concentration that appears to give higher gene expression leading to the better immune responses.

|  | 2 weeks | | | 4 weeks | | |
| --- | --- | --- | --- | --- | --- | --- |
|  | DNA alone | P85 0.01% | P85 0.1% | DNA alone | P85 0.01% | P85 0.1% |
| pCMV-Bgal DNA 5 µg | | | | | | |
| Responding mice (%) | 16 | 66 | 0 | 50 | 100 | 33 |
| Average Titer of responding mice | 1:2000 | 1:3000 | 0 | 1:2800 | 1:16000 | 1:1000 |
| pCMV-Bgal DNA 50 µg | | | | | | |
| Responding mice (%) | 33 | 66 | 100 | 33 | 66 | 100 |
| Average Titer of responding mice | 1:1000 | 1:4000 | 1:1250 | 1:8000 | >1:16000 | >1:16000 |

EXAMPLE 55

A Single Block Copolymer Improves the Humoral Immune Response to DNA Compositions Administered Intramuscularly In this experiment, C57B1/mice showed an improved immune response following intramuscular injection with a DNA composition. C57BI/57 (6-7 week-old) female mice were injected intramuscularly with 5 and 50 ug of pCMV-Bgal with and without PLURONIC®85. Six mice were injected with each sample formulation. The formulation was prepared as described in Example 51. Blood samples were collected 2 and 4 weeks after innoculation to monitor the humoral immune response specific to galactosidase. The detection of specific anti-β-galactosidase antibodies was determined by means of an ELISA as described in Example 52.

The data are expressed as the percentage of mice responding to the antigen and the average titers of the responding mice. The data demonstrate that after 2 weeks, none of the mice injected with 5 ug of pCMV-Bgal alone showed an immune response. However, all mouse injected with pCMV-Bgal formulated with PLURONIC®85 showed an immune response. The anti-β-galactosidase antibody titers of mice injected with pCMV-Bgal formulated with PLURONIC®85 were always higher than the mice injected with pCMV-Bgal alone.

| pCMV-Bgal DNA 5 µg | | | | | | |
| --- | --- | --- | --- | --- | --- | --- |
|  | 2 weeks | | | 4 weeks | | |
|  | DNA alone | P85 0.01% | P85 0.1% | DNA alone | P85 0.01% | P85 0.1% |
| Responding mice (%) | 0 | 100 | 33 | 100 | 100 | 100 |
| Average Titer of responding mice | 0 | 1:1500 | 1:1000 | 1:4000 | >1:16000 | >1:16000 |

| pCMV-Bgal DNA 50 µg | | | | | | |
| --- | --- | --- | --- | --- | --- | --- |
|  | 2 weeks | | | 4 weeks | | |
|  | DNA alone | P85 0.01% | P85 0.1% | DNA alone | P85 0.01% | P85 0.1% |
| Responding mice (%) | 100 | 100 | 100 | 100 | 100 | 100 |
| Average Titer of responding mice | 1:2000 | 1:9000 | 1:7000 | 1:4000 | >1:16000 | >1:16000 |

EXAMPLE 56

A Combination of Block Copolymers Improved the Humoral Immune Response to DNA Compositions Administered Intramuscularly In this experiment, block copolymers are used to improve the humoral immune response in muscle (tibialis anterior) of C57B1/57 (6-7 week-old) female mice kept in groups of 7. C57BI/57 mice were injected intramuscularly with 5 or 50 ug of pCMV-Bgal with or without a combination of block copolymers. The formulation was prepared as described in Example 51. Blood samples were collected after 2 and 4 weeks to monitor the humoral immune response specific to galactosidase. The detection of specific antibodies was determined by means of an ELISA as described in Example 52.

The data are expressed as the percentage of mice responding to the antigen and the average titers of responding mice. The data demonstrate that when mice receive the DNA formulated with the block copolymers: (1) an additional injection or booster is not needed; (2) that less DNA is required to immunize the mice; and (3) the time to develop the immune response is shorter.

|  | Percentage of responders(Average titers) | |
|---|---|---|
|  | 2 weeks | 4 weeks |
| Formulation5 ug DNA | | |
| PCMV-Bgal | 16(1:333) | 83(1:2000) |
| pCMV-B-gal + PLURONIC ® F127/L61 | 100(1:2000) | 100(1:4000) |
| Formulation50 ug DNA | | |
| PCMV-Bgal | 33(1:666) | 100(1:4000) |
| pCMV-B-gal + PLURONIC ® F127/L61 | 100(1:3000) | 100(1:4000) |

EXAMPLE 57

A Combination of Block Copolymers Improves the Humoral Immune Response to a Protective Surface Antigen of the PRRSV Virus in Pigs and Mice Pigs and Balb/C, CD1 mice (at least 5 animals and all female) were injected intradermally with an adenovirus containing the ORF5 gene of the PRRSV virus (encoding_the GP5 protein) with or without a combination of block copolymers (PLURONIC®_F127/L61) on days 0 and 21. The formulation was prepared as described in Example 51. Fifty days later the animals were challenged with the PRRSV virus. Blood samples were collected at 7 days post-challenge to monitor the humoral immune response specific to GP5.

The results demonstrated that only the animals that received the adenovirus formulated with PLURONIC® F127/L61 developed an immunological memory as demonstrated by Western-blot against GP5.

EXAMPLE 58

Solution Behavior of Poly(oxyethylene)-Poly(oxypropylene) Block Copolymers

Poly(oxyethylene)-poly(oxypropylene) block copolymers were dissolved in the phosphate-buffered saline, 10 μM, pH 7.4 (PBS) or in 2.5% solution of bovine serum albumin (BSA) in PBS at the concentrations shown below, and the mixtures incubated for at least one hour at 22.5° C. or 37° C. The effective diameters of the aggregates formed in these systems were then measured by quasielastic light scattering method as described by Kabanov et al., *Macromolecules* 28:2303-2314 (1995). The results were as follows:

| Copolymer | Conc., % | T, °C. | Effective diameter, nm −BSA | Effective diameter, nm +BSA | Comments |
|---|---|---|---|---|---|
| Pluronic L61 | 0.05 | 22.5 | ND | 10.6 | |
| | 0.1 | 22.5 | ND | 23.4 | |
| | 0.25 | 22.5 | ND | 48.8 | |
| | 0.5 | 22.5 | ND | 138.3 | |
| | 0.005 | 37 | ND | 138 | |
| Pluronic L61 | 0.006 | 37 | ND | — | |
| | 0.008 | 37 | 336 | — | |
| | 0.01 | 37 | 455 | 120 | |
| | 0.025 | 37 | 960 | (*) | |
| | 0.04 | 37 | | (*) | |
| | 0.05 | 37 | 1265 | (*) | |
| | 0.075 | 37 | 1120 | (*) | |
| | 0.1 | 37 | LPS | LPS | |
| | 0.25 | 37 | LPS | LPS | |
| | 0.5 | 37 | LPS | LPS | |
| Pluronic L81 | 0.04 | 22.5 | — | 13.8 | |
| | 0.1 | 22.5 | ND | 20.6 | |
| | 0.25 | 22.5 | ND | 379 | Very cloudy solution with BSA |
| | 0.5 | 22.5 | 935 | — | Very cloudy Solutions |
| | 0.01 | 37 | — | 266 | |
| | 0.04 | 37 | 1004 | (*) | |
| | 0.06 | 37 | (*) | (*) | |
| | 0.08 | 37 | (*) | (*) | |
| Pluronic L121 | 22.5 | 0.01 | — | 541.5 | |
| | 22.5 | 0.05 | — | 330 | |
| Pluronic F44 | 22.5 | 0.5 | ND | 12.9 | |
| | 22.5 | 1.0 | ND | 11.7 | |
| | 22.5 | 2.25 | ND | 14.2 | |
| | 22.5 | 4.5 | ND | 28.7 | |
| | 22.5 | 7.5 | ND | — | |
| | 22.5 | 10.0 | ND | 105 | |
| | 37 | 0.5 | ND | 84.4 | |
| | 37 | 1.0 | ND | 97.1 | |
| | 37 | 2.25 | ND | 137 | |
| | 37 | 5.0 | ND | 68.1 | |
| | 37 | 7.5 | ND | | |
| | 37 | 10.0 | 12.3 | 69.4 | |
| Pluronic L64 | 0.5 | 22.5 | ND | 10.8 | |
| | 1.0 | 22.5 | ND | 12 | |
| | 5.0 | 22.5 | ND | 21.6 | Opalescence and small fraction of aggregates (85 nm) with BSA |
| | 0.1 | 37 | ND | 36.2 | |
| | 0.5 | 37 | 240 | 192.5 | Slightly cloudy solution without BSA and very cloudy solution with BSA |
| | 1.0 | 37 | 16.6 | 11.6 | |
| | 5.0 | 37 | 13.1 | 11.3 | |
| Pluronic P85 | 22.5 | 0.5 | ND | — | |
| | 22.5 | 1.0 | ND | 12.9 | |
| | 22.5 | 5.0 | ND | 18.7 | |
| | 37 | 0.5 | 13.9 | — | |
| | 37 | 1.0 | 12.6 | 79.6 | |
| | 37 | 5.0 | 12.8 | 109 | |
| Pluronic F108 | 37 | 2.0 | — | 22.8 | — |
| Pluronic | 37 | 1.0 | — | 23.2 | — |

-continued

| Copolymer | Conc., % | T, °C. | Effective diameter, nm | | Comments |
|---|---|---|---|---|---|
| | | | −BSA | +BSA | |
| F127 | 37 | 2.0 | — | 21.5 | — |
| Tetronic T1307 | 22.5 | 2.0 | — | ND | — |
| | 37 | 0.5 | — | 16.7 | — |
| | 37 | 1.0 | — | 17.1 | — |
| | 37 | 2.0 | — | 16.6 | 37.4 |

"ND": Non Detectable
"LPS": Liquid Phase Separation.
(*)Turbidity too high for light scattering measurements.

These results suggest that (1) hydrophobic poly(ethyleneoxide)-poly(propyleneoxide) block copolymers with propylene oxide content not less than 50% (w/v) reveal tendency for aggregation in aqueous solutions at physiological temperature, (2) aggregation and phase separation of these copolymers is significantly enhanced in the presence of serum proteins.

EXAMPLE 59

Effects of Hydrophilic Pluronic Copolymers on Solution Behavior of Hydrophobic Pluronic Copolymers The same procedure as in Example 58, but substituting a mixture of two different poly(ethylene oxide)-poly(propylene oxide) block copolymers for the single copolymer. The results were as follows:

| First Copolymer (conc. %) | Second conc., % | T, ° C. | Effective diameter, nm | |
|---|---|---|---|---|
| | | | −BSA | +BSA |
| Pluronic L121 | Pluronic F127(0.5) | 22.5 | 116.4 | |
| | Pluronic F127(1.0) | 22.5 | 113.9 | |
| | Pluronic F127(5.0) | 22.5 | 313.2 | |
| | Pluronic F127(0.5) | 37 | 88.7 | |
| Pluronic L121(0.1) | Pluronic F127(1.0) | 37 | 77.1 | |
| | Pluronic F127(2.0) | 37 | 177 | |
| | Pluronic F127(5.0) | 37 | 262 | |
| Pluronic L61(0.1) | Pluronic F127(0.5) | 37 | 26.7 | 23.8 |
| | Pluronic F127(1.0) | 37 | 23.6 | 12.9 |
| | Pluronic F127(2.0) | 37 | 21.6 | 13.8 |
| Pluronic L61(0.125) | Pluronic F127(1.0) | 37 | 24.7 | 53 |
| | Pluronic F127(2.0) | 37 | 22.3 | — |
| Pluronic L61 (0.25) | Pluronic F127(0.5) | 37 | (*) | — |
| | Pluronic F127(1.0) | 37 | (*) | — |
| | Pluronic F127(2.0) | 37 | 22.4 | 15.0 |
| Pluronic L61(0.25) | Pluronic F108(2.0) | 37 | 840 | — |
| Pluronic L61(0.1) | Tetronic T1307(1.0) | 37 | (*) | — |
| | Tetronic T1307(1.5) | 37 | 915.4 | — |
| | Tetronic T1307(2.0) | 37 | 16.3 | 624.8 |
| Pluronic L61(0.15) | Tetronic T1307(2.0) | 37 | 387.4 | — |
| Pluronic L61(0.2) | | 37 | 520 | — |
| Pluronic L61(0.25) | | 37 | 735.3 | — |
| Pluronic L61(0.1) | Tetronic T1307(2.5) | 37 | — | 522.3 |
| | Tetronic T1307(3.0) | 37 | | 225 |
| | Tetronic T1107(2.0) | 37 | (*) | |

"ND": Non-Detectable.
(*)Turbidity too high for light scattering measurements.

These results suggest that, (1) hydrophilic poly(oxyethylene)-poly(oxypropylene) block copolymers with ethylene oxide content more than 50% (w/v) prevent aggregation of hydrophobic hydrophilic Poly(oxyethylene)-poly(oxypropylene) block copolymers with propylene oxide content not less than 50% (w/v) at physiological temperatures; (2) hydrophilic poly(oxyethylone)-poly(oxypropylene) block copolymers with ethylene oxide content more than 50% (w/v) prevent aggregation of hydrophobic hydrophilic poly(oxyethylene)-poly(oxypropylene) block copolymers with propylene oxide content not less than 50% in the presence of serum proteins. These data also show that when a mixture of block copolymers is used hydrophillic block copolymer with ethylene oxide content of 70% or more is preferred, and PLURONIC®F127 is particularly preferred.

EXAMPLE 60

Isolation of the Infiltrating Cells From Muscle Injected with pCMV-βgal/PLURONIC F127/PLURONIC L61

C57/B1/6 mice were injected i.m. with 50 μg of pCMV-βgal in 50 μl of saline or 50 μg of pCMV/bgal in 50 μl of the solution containing a mixture of PLURONIC F127 and PLURONIC L61. The mixture of PLURONIC F127 and PLURONIC L61 was prepared as described in Example 51 at the block copolymer w:w ratio of 8:1 (F127:L61). Five days following the injection, muscles were either frozen in order to be sliced to perform a histoimmunochemistry study or harvested to isolate mechanically infiltrating cells. Muscle sections were then stained with x-gal and hematoxilin-eosin to locate and evaluate the extent of gene expression and the amount of infiltrating cells. The results demonstrated that muscles injected with pCMV-βgal/PLURONIC F127/ PLURONIC L61 had 10 times higher x-gal staining, a proportionally more infiltrating leukocites was found in the transgene expression areas of the tissue in the case of formulated DNA compared to naked pCMV-βgal. The muscle sections were then used to perform an immunohistochemistry analysis in order to determine the cell type infiltrating leukocytes the muscle following the injection. In addition, the infiltrating cells were extracted from the muscles to perform flow cytometry studies. Antibodies against CD3, CD4, CD8 and CD11a molecular markers were chosen to determine if the isolated cells were T-cells, antibody against B220 molecule was chosen to determine if the cells were B-cells, antibody against NK1.1 molecule were used to determine if the cells were natural killer cells, antibody against Gr-1 marker were used to determine if the cells were infiltrating neutrophils, and antibody against Mac-1 molecule were used to determine if the cells were macrophages. The results of these studies revealed that the majority of the isolated cells did not expressed any of the marker antigens tested. The only known infiltrating cells that do not express the above surface markers (see results below) are immature dendritic cells.

Phenotyping of the infiltrating cells in muscle injected with pCMV-βgal/PLURONIC F127/PLURONIC L61.

| Surface markers | Immunohisto chemistry Results (% of stained cells) | Flow Cytometry Results (% of stained cells) | Positive control in flow cytometry (% of stained splenocytes) |
|---|---|---|---|
| CD3 | N.D. | 1.2 | 41 |
| CD4 | 0 | 0 | 22 |
| CD8 | 0 | 0 | 12 |
| CD11a | N.D. | 3 | 98 |
| GR-1 | 0 | 1.5 | 2 |
| Mac-1 | N.D. | 3 | 92 |
| NK1.1 | N.D. | 2 | 4 |
| B220 | N.D. | 0 | 56 |

EXAMPLE 61

Phenotype Identification of the Infiltrating Cells

Cells from the muscles of mice injected with PLURONIC F127/PLURONIC L61 alone, pCMVβgal, pCMVβgal/PLURONIC F127/PLURONIC L61, pCMV (empty vector) and empty vector/PLURONIC F127/PLURONIC L61 were isolated and cultured in conditions favoring the growth of dendritic cells. More specifically, the equal amounts of cells from the above groups were plated in a 96-well plate. After 7 days under constant stimulation with GM-CSF (growth factor known to activate the differentiation of DCs), GM-CSF+IL-4 and LPS (also known to be a stimulant of DCs), only cells isolated from the muscles injected with pCMVβgal/PLURONIC F127/PLURONIC L61 were growing and exhibiting dendrites (spikes and veils) (see results below).

| Cell Growth Following a 7-Day Stimulation. | | | |
|---|---|---|---|
|  | GM-CSF (confluence after 12 days) | LPS (confluence after 12 days) | GM-CSF + IL-4 (confluence after 12 days) |
| PLURONIC F127/PLURONIC L61 | — | — | — |
| pCMVβgal | — | — | — |
| pCMVβgal/PLURONIC F127/PLURONIC L61 | 50% | 20% | 90% |
| empty vector | — | — | — |
| empty vector/PLURONIC F127/PLURONIC L61 | — | — | 10% |

EXAMPLE 62

Promoter Dependence Effect of PLURONIC F127/PLURONIC L61

In this experiment, PLURONIC F127/PLURONIC L61 was used to test its effect on gene expression (transcription) in muscle (tibialis anterior) of C57B1/6 (6-7 week-old) female mice kept by groups of 4 and fed ad libidum. Five μg of CMV-, 5V40-, AP-1, NF-kB-driven plasmid DNAs encoding for luciferase are formulated with and without PLURONIC F127/PLURONIC L61 and injected intramuscularly into the tibialis anterior muscle. Before each injection, the mice are anesthetized with a mixed solution of ketamine and xylazine. Mice are sacrificed 5 days following the injection and each injected muscle is dissected and rapidly homogenized with a polytron in cell lysis buffer (Promega Corporation) supplemented with protease inhibitors. The extracts are kept on ice for 30 minutes and then centrifuged at a maximum speed for 2 minutes. The supernatents are kept and analyzed for luciferase activity. The assay is done as follows: 20 μl of supernatent is added to luminometric tubes containing 100 μl of luciferase substrate (Promega Corporation). Light emission is measured with a luminometer (Berthold) for a period of 5 seconds. The data is initially in relative light units per second per tibialis anterior but then reported in percentage of increase over naked DNA. As shown in the table below, PLURONIC F127/PLURONIC L61 has a promoter dependence leading to differential transcription.

| Conditions | % of increase over naked DNA |
|---|---|
| pCMV-Luc in saline | 100 |
| pCMV-Luc in PLURONIC F127/PLURONIC L61 @ 0.01% w/v | 1000 |
| pSV4O-Luc in saline | 100 |
| pSV4O-Luc in PLURONIC F127/PLURONIC L61 @ 0.01% w/v | 250 |
| pNF-kB-Luc in saline | 100 |
| pNF-kB-Luc in PLURONIC F127/PLURONIC L61 @ 0.01% w/v | 700 |
| pAP-1-Luc in saline | 100 |
| pAP-1-Luc in PLURONIC F127/PLURONIC L61 @ 0.01% w/v | 90 |

EXAMPLE 63

PLURONIC F127/PLURONIC L61 Increases Antigen Uptake in Infiltrating Cells (Dendritic Cells)

The tibialis anterior muscles were harvested 5 days post-injection (50 μg/muscle), dissected out, and minced by mechanical force in 2 ml of complete RPMI. The suspension of small pieces of muscles was stirred with a magnetic bar for 10 minutes to extract the infiltrating cells. The extracted cells were recovered by filtering them through a funnel with a sterile glass wool plug. The remaining pieces of muscles were extracted 2 more times by adding 2 ml of complete medium and by repeating the above procedure. The cells suspensions were pooled and centrifuged for 10 minutes at 1200 rpm at 4° C. The cell pellet was resuspended in order to get a cell density of $1 \times 10^6$ cells per eppendorf tube. The cells are then extracted in lysis buffer for 30 minutes and then centrifuged at a maximum speed for 2 minutes. The supernatents are kept and analyzed for luciferase activity. The assay is done as follows: 20 µl of supernatent are added to luminometric tubes containing 100 µl of luciferase substrate (Promega Corporation). Light emission is measured with a luminometer (Berthold) for a period of 5 seconds. The data is reported in relative light units per second per tibialis anterior.

| Samples | RLU/s per 1 x 106 cells |
|---|---|
| DC isolated from muscles injected with CMV-Luc in saline | 272 ± 50 |
| DC isolated from muscles injected with pCMV-Luc formulated with PLURONIC F127/PLURONIC L61 @ 0.01 w/v | 3155 ± 360 |

There will be various modifications, improvements, and applications of the disclosed invention that will be apparent to those of skill in the art, and the present application is intended to cover such embodiments. Although the present invention has been described in the context of certain preferred embodiments, it is intended that the full scope of these be measured by reference to the scope of the following claims.

The disclosures of various publications, patents and patent applications that are cited herein are incorporated by reference in their entireties.

---

What is claimed is:

1. A method of inducing activation of dendritic cells comprising administering a composition to a mammal, wherein the composition comprises at least one polynucleotide and at least one polyoxyethylene-polyoxypropylene block copolymer and a polycationic polymer, wherein a polynucleotide complex is formed between the polynucleotide, block copolymer and polycationic polymer, wherein the block copolymer comprises at least F127 and L61, and wherein more than one gene is expressed by the polynucleotide, and wherein at least one expresses an antigen and at least one expresses a molecule that activates dendritic cells.

2. The method of claim 1, wherein the block copolymer is present in amounts insufficient for gel formation.

3. A method of inducing activation of dentritic cells comprising administering a composition to a mammal, wherein the composition comprises at least one polynucleotide and at least one polyoxyethylene-polyoxypropylene block copolymer and a polycationic polymer, wherein a polynucleotide complex is formed between the polynucleotide, block copolymer and polycationic polymer, wherein the at least one polyoxyethylene-polyoxypropylene block copolymer comprises F127 and L61, wherein the composition forms a molecular solution or colloidal dispersion, wherein the at least one polynucleotide comprises a CMV promoter or a NF-κB-sensitive element, and wherein more than one gene is expressed, and wherein at least one expresses an antigen and at least one expresses a molecule that activates dendritic cells.

4. A method of increasing an immune response comprising administering a composition to a mammal, wherein the composition comprises at least one polynucleotide and at least one polyoxyethylene-polyoxypropylene block copolymer and a polycationic polymer, wherein a polynucleotide complex is formed between the polynucleotide, block copolymer and polycationic polymer, wherein the at least one polyoxyethylene-polyoxypropylene block copolymer comprises F127 and L61, wherein more than one gene is expressed, and wherein at least one expresses an antigen and an adjuvant is expressed from the at least one polynucleotide thereby inducing an immune response.

5. The method of claim 4, wherein the composition is administered orally, topically, rectally, vaginally, parenterally, intramuscularly, intradermally, subcutaneously, intraparitoneally, or intravenously.

6. The method of claim 5, wherein the composition is administered intramuscularly.

7. The method of claim 6, wherein said composition is administered to at least one of smooth, skeletal, and cardiac muscles.

8. The method of claim 5, wherein the composition is administered intradermally.

9. The method of inducing activation of dendritic cells of claim 1 wherein the composition forms a molecular solution or colloidal dispersion.

10. The method of claim 9, wherein the composition is administered orally, topically, rectally, vaginally, parenterally, intramuscularly, intradermally, subcutaneously, intraparitoneally, or intravenously.

11. The method of claim 9, wherein said composition is administered to at least one of smooth, skeletal, and cardiac muscles.

12. The method of claim 10, wherein the composition is administered intradermally.

* * * * *

SEQUENCE LISTING

```
<160> NUMBER OF SEQ ID NOS: 7

<210> SEQ ID NO 1
<211> LENGTH: 10
<212> TYPE: DNA
<213> ORGANISM: Artificial Sequence
<220> FEATURE:
<223> OTHER INFORMATION: consensus sequence for kB prpomoter
<220> FEATURE:
<221> NAME/KEY: misc_feature
<222> LOCATION: (5)..(6)
<223> OTHER INFORMATION: n at positions 5 and 6 is a, c, g or t

<400> SEQUENCE: 1 gggrnnyccc                                                          10

<210> SEQ ID NO 2
<211> LENGTH: 17
<212> TYPE: DNA
<213> ORGANISM: Human immunodeficiency virus

<400> SEQUENCE: 2
ggctccattt cttgctc                                                  17

<210> SEQ ID NO 3
<211> LENGTH: 17
<212> TYPE: DNA
<213> ORGANISM: Homo sapiens

<400> SEQUENCE: 3
ccttcaagat ccatccc                                                  17

<210> SEQ ID NO 4
<211> LENGTH: 12
<212> TYPE: DNA
<213> ORGANISM: herpes simplex virus

<400> SEQUENCE: 4
cgttcctcct gu                                                       12
```

```
<210> SEQ ID NO 5
<211> LENGTH: 12
<212> TYPE: DNA
<213> ORGANISM: Influenza virus

<400> SEQUENCE: 5
agcaaaagca gg                                                        12

<210> SEQ ID NO 6
<211> LENGTH: 17
<212> TYPE: DNA
<213> ORGANISM: Human immunodeficiency virus

<400> SEQUENCE: 6
ggctccattt cttgctc                                                   17

<210> SEQ ID NO 7
<211> LENGTH: 12
<212> TYPE: DNA
<213> ORGANISM: Herpes Simplex Virus type 1

<400> SEQUENCE: 7
ggttcctcct gu                                                        12
```